US008939914B2

(12) United States Patent
Turnquist et al.

(10) Patent No.: US 8,939,914 B2
(45) Date of Patent: Jan. 27, 2015

(54) RADIOMETERS AND RELATED DEVICES AND METHODS

(75) Inventors: Douglas G. Turnquist, Taylorsville, UT (US); Doug Reudink, Port Townsend, WA (US); Brent W. Snow, Salt Lake City, UT (US)

(73) Assignee: Thermimage, Inc., Taylorsville, UT (US)

( * ) Notice: Subject to any disclaimer, the term of this patent is extended or adjusted under 35 U.S.C. 154(b) by 446 days.

(21) Appl. No.: 13/225,319

(22) Filed: Sep. 2, 2011

(65) Prior Publication Data

US 2012/0053445 A1 Mar. 1, 2012

Related U.S. Application Data

(63) Continuation-in-part of application No. 12/713,099, filed on Feb. 25, 2010, and a continuation-in-part of application No. 12/713,114, filed on Feb. 25, 2010, now abandoned.

(Continued)

(51) Int. Cl.
*A61B 5/00* (2006.01)
*A61B 5/01* (2006.01)
*A61B 18/18* (2006.01)
(Continued)

(52) U.S. Cl.
CPC ............... *A61B 5/01* (2013.01); *A61B 5/6804* (2013.01); *A61B 5/6887* (2013.01); *A61B 18/1815* (2013.01); *A61B 5/0507* (2013.01); *A61B 5/202* (2013.01); *A61B 5/4547* (2013.01); *A61B 2018/00023* (2013.01); *A61B 2018/00791* (2013.01); *A61B 2562/0228* (2013.01);
(Continued)

(58) Field of Classification Search
CPC ........... A61B 5/01; A61B 2017/00084; A61B 2017/00088; A61B 2017/00092; A61B 2017/00097; A61B 2017/00101; A61B 2018/00791; A61B 2018/00797; A61B 2018/00803; A61B 2018/00809; A61B 2018/00815; A61B 2018/00821; G01K 13/002; G01K 13/004
USPC .................. 600/549, 587, 595; 374/158, 163
See application file for complete search history.

(56) References Cited

U.S. PATENT DOCUMENTS 3,581,570 A  6/1971  Wortz
4,140,130 A  2/1979  Storm, III
(Continued)

FOREIGN PATENT DOCUMENTS

JP    05293086 A    9/1993
JP    2004073908 A   11/2004
(Continued)

OTHER PUBLICATIONS

Office Action mailed Jun. 8, 2011 in U.S. Appl. No. 12/713,114, filed Feb. 25, 2010.

*Primary Examiner* — Adam Eiseman
(74) *Attorney, Agent, or Firm* — Phillips Ryther & Winchester; Matthew D. Thayne

(57) ABSTRACT

Certain radiometer assemblies can include an antenna that is shielded within an enclosure, which can have an open end. The antenna can be used to receive signals from a patient via a matching layer that is positioned at the open end of the enclosure. In some assemblies, a rim of shielding material encompasses the open end of the enclosure so as to reduce stray electromagnetic interference, such as when the assembly is used to monitor a deep tissue temperature.

16 Claims, 11 Drawing Sheets

Related U.S. Application Data

(60) Provisional application No. 61/156,444, filed on Feb. 27, 2009, provisional application No. 61/156,441, filed on Feb. 27, 2009, provisional application No. 61/156,438, filed on Feb. 27, 2009, provisional application No. 61/156,433, filed on Feb. 27, 2009, provisional application No. 61/156,427, filed on Feb. 27, 2009, provisional application No. 61/156,407, filed on Feb. 27, 2009, provisional application No. 61/156,401, filed on Feb. 27, 2009, provisional application No. 61/156,393, filed on Feb. 27, 2009, provisional application No. 61/156,382, filed on Feb. 27, 2009.

(51) Int. Cl.
  *A61B 5/05* (2006.01)
  *A61B 5/20* (2006.01)
  *A61B 18/00* (2006.01)

(52) U.S. Cl.
  CPC ..... *A61B2562/0271* (2013.01); *A61B 2562/04* (2013.01); *A61B 2562/182* (2013.01)
  USPC ........................................................ 600/549

(56) References Cited

U.S. PATENT DOCUMENTS

| | | | |
|---|---|---|---|
| 4,513,750 A | 4/1985 | Heyman et al. | |
| 4,557,272 A | 12/1985 | Carr | |
| 4,605,012 A | 8/1986 | Ringeisen et al. | |
| 4,647,281 A | 3/1987 | Carr | |
| 4,798,215 A | 1/1989 | Turner | |
| 5,255,979 A * | 10/1993 | Ferrari | 374/158 |
| 5,275,594 A | 1/1994 | Baker et al. | |
| 5,370,121 A | 12/1994 | Reichenberger et al. | |
| 5,496,271 A | 3/1996 | Burton et al. | |
| 5,503,150 A | 4/1996 | Evans | |
| 5,542,915 A | 8/1996 | Edwards et al. | |
| 5,628,771 A | 5/1997 | Mizukawa et al. | |
| 5,660,836 A | 8/1997 | Knowlton | |
| 5,685,839 A | 11/1997 | Edwards et al. | |
| 5,797,398 A | 8/1998 | Bowman | |
| 5,833,625 A | 11/1998 | Essen-Moller | |
| 5,913,886 A | 6/1999 | Soloman | |
| 5,935,075 A | 8/1999 | Casscells et al. | |
| 5,954,668 A | 9/1999 | Uber, III et al. | |
| 6,245,094 B1 | 6/2001 | Pompei | |
| 6,329,655 B1 * | 12/2001 | Jack et al. | 250/338.1 |
| 6,330,479 B1 | 12/2001 | Stauffer | |
| 6,347,251 B1 | 2/2002 | Deng | |
| 6,475,159 B1 | 11/2002 | Casscells et al. | |
| 6,615,071 B1 | 9/2003 | Casscells, III et al. | |
| 6,773,159 B2 | 8/2004 | Kim et al. | |
| 7,217,245 B1 * | 5/2007 | Snow et al. | 600/549 |
| 7,263,398 B2 | 8/2007 | Carr | |
| 7,354,195 B2 * | 4/2008 | Sakano | 374/208 |
| 2002/0126731 A1 | 9/2002 | Stergiopoulos et al. | |
| 2002/0183621 A1 | 12/2002 | Pfeiffer et al. | |
| 2003/0130575 A1 | 7/2003 | Desai | |
| 2004/0215098 A1 * | 10/2004 | Barton et al. | 600/549 |
| 2004/0249272 A1 | 12/2004 | Carr | |
| 2005/0245839 A1 * | 11/2005 | Stivoric et al. | 600/549 |
| 2005/0267382 A1 * | 12/2005 | Church et al. | 600/549 |
| 2007/0196282 A1 | 8/2007 | Oliver | |
| 2009/0012417 A1 | 1/2009 | Carr | |
| 2009/0275808 A1 * | 11/2009 | DiMaio et al. | 600/301 |
| 2010/0069782 A1 | 3/2010 | Icove et al. | |
| 2010/0222699 A1 | 9/2010 | Turnquist et al. | |
| 2010/0222776 A1 | 9/2010 | Turnquist et al. | |
| 2011/0051776 A1 * | 3/2011 | Bieberich et al. | 374/163 |

FOREIGN PATENT DOCUMENTS

| | | |
|---|---|---|
| JP | 208099996 A | 1/2008 |
| WO | WO 00/07665 A1 | 2/2000 |
| WO | WO 2005/112179 A2 | 11/2005 |

* cited by examiner

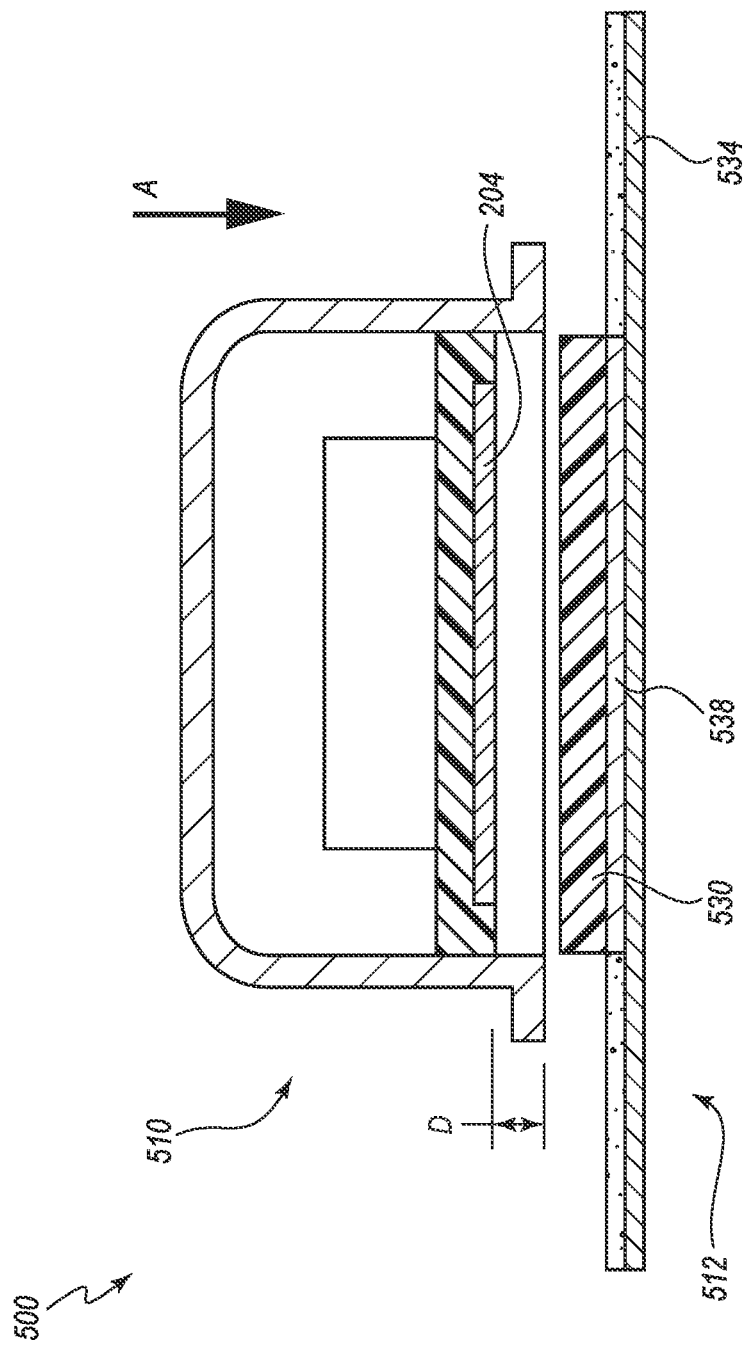

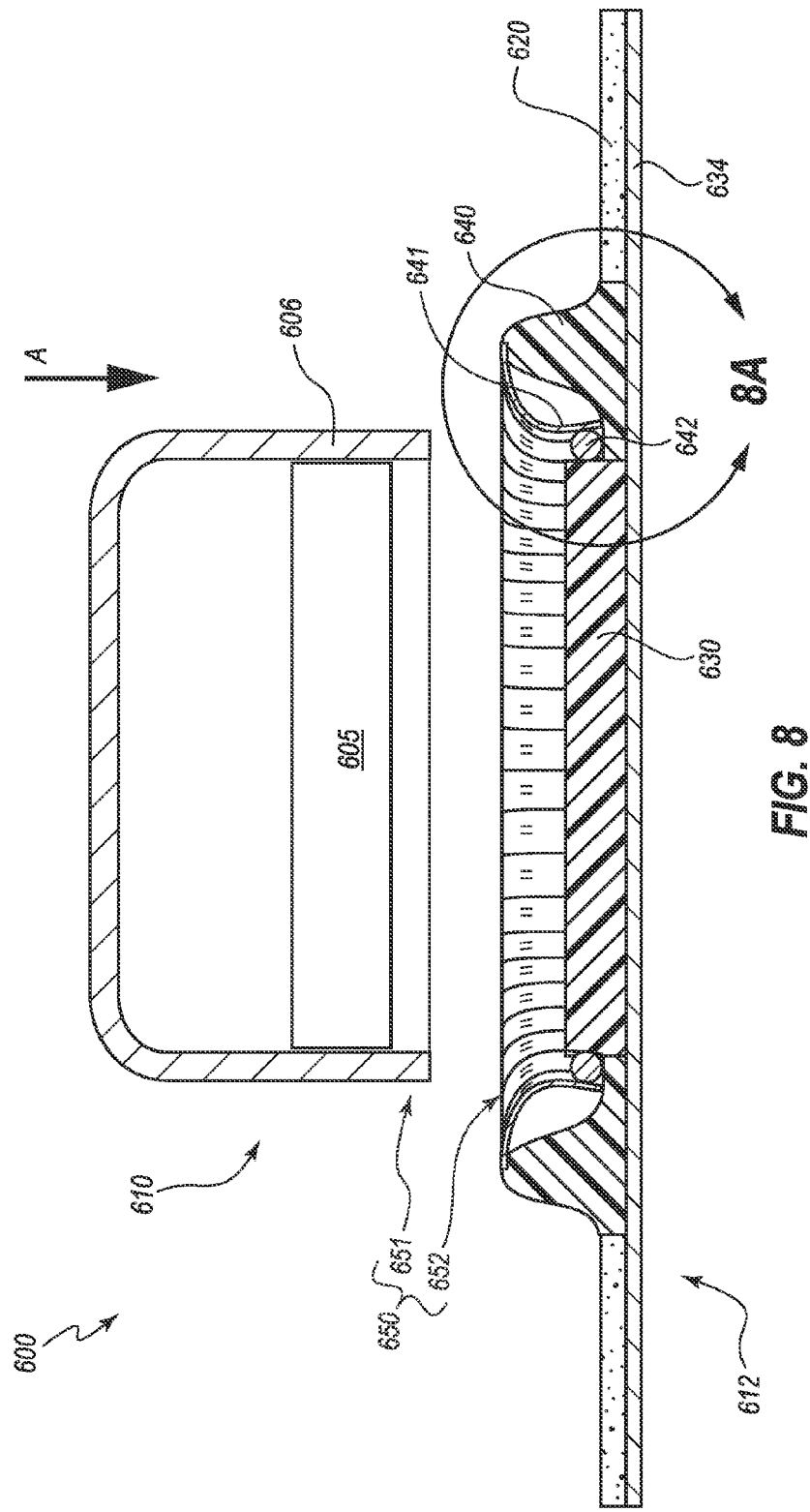

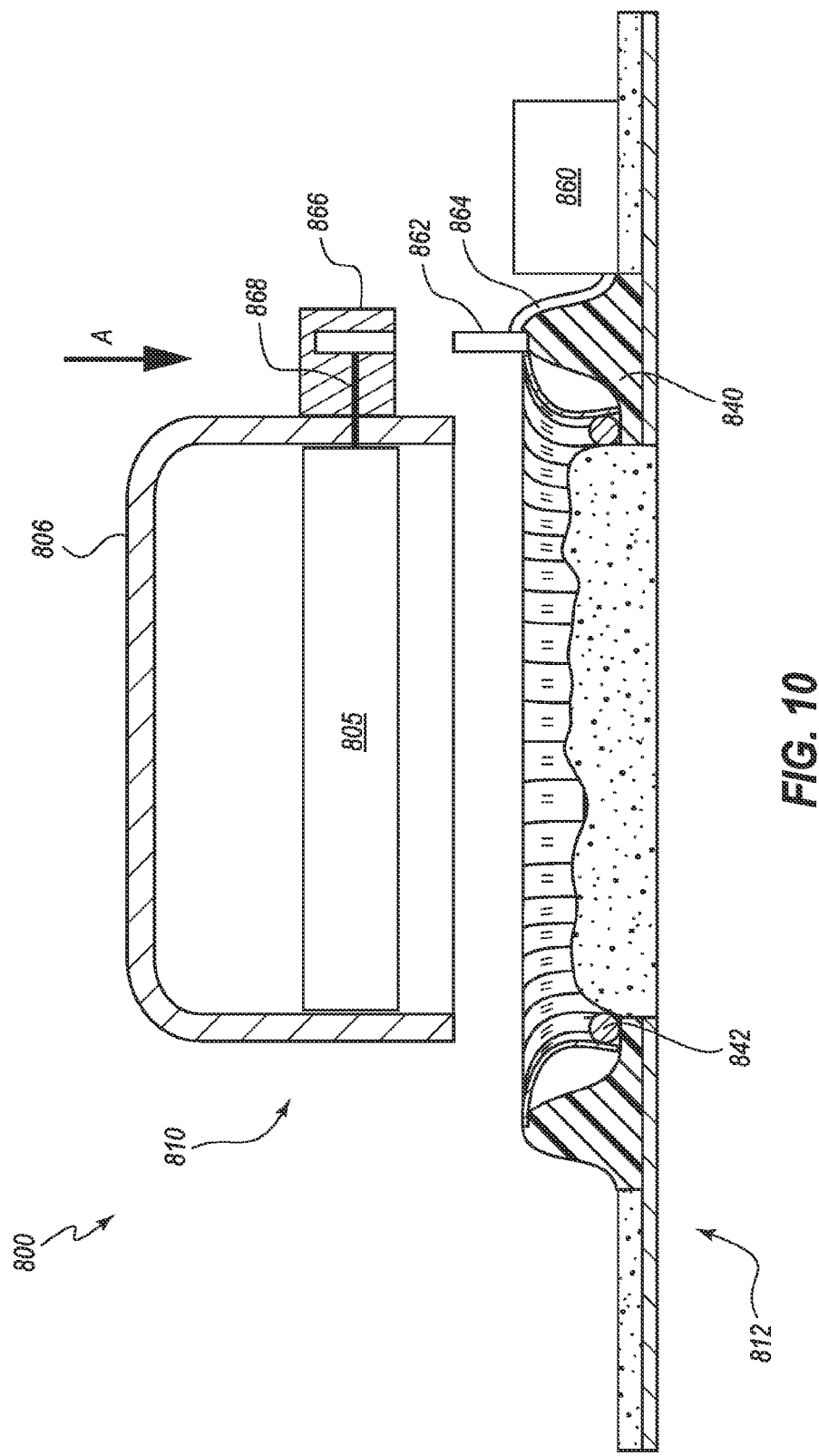

RADIOMETERS AND RELATED DEVICES AND METHODS

CROSS-REFERENCE TO RELATED APPLICATIONS

This application is a continuation-in-part of prior U.S. patent application Ser. No. 12/713,099, filed on Feb. 25, 2010, titled MONITORING SYSTEM, which published as U.S. Patent Application Publication No. 2010/0222776 on Sep. 2, 2010, and which claims the benefit of U.S. Provisional Patent Application No. 61/156,444, filed Feb. 27, 2009, U.S. Provisional Patent Application No. 61/156,441, filed Feb. 27, 2009, U.S. Provisional Patent Application No. 61/156,438, filed Feb. 27, 2009, U.S. Provisional Patent Application No. 61/156,433, filed Feb. 27, 2009, U.S. Provisional Patent Application No. 61/156,427, filed Feb. 27, 2009, U.S. Provisional Patent Application No. 61/156,407, filed Feb. 27, 2009, U.S. Provisional Patent Application No. 61/156,401, filed Feb. 27, 2009, U.S. Provisional Patent Application No. 61/156,393, filed Feb. 27, 2009, and U.S. Provisional Patent Application No. 61/156,382, filed Feb. 27, 2009; and this application is a continuation-in-part of prior U.S. patent application Ser. No. 12/713,114, filed on Feb. 25, 2010, titled METHOD FOR MONITORING INTERNAL TISSUE, which published as U.S. Patent Application Publication No. 2010/0222699 on Sep. 2, 2010, and which claims the benefit of U.S. Provisional Patent Application No. 61/156,444, filed Feb. 27, 2009, U.S. Provisional Patent Application No. 61/156,441, filed Feb. 27, 2009, U.S. Provisional Patent Application No. 61/156,438, filed Feb. 27, 2009, U.S. Provisional Patent Application No. 61/156,433, filed Feb. 27, 2009, U.S. Provisional Patent Application No. 61/156,427, filed Feb. 27, 2009, U.S. Provisional Patent Application No. 61/156,407, filed Feb. 27, 2009, U.S. Provisional Patent Application No. 61/156,401, filed Feb. 27, 2009, U.S. Provisional Patent Application No. 61/156,393, filed Feb. 27, 2009, and U.S. Provisional Patent Application No. 61/156,382, filed Feb. 27, 2009. The entire contents of each of the foregoing applications and publications is hereby incorporated by reference herein.

TECHNICAL FIELD

This application relates generally to radiometers and related devices and methods, and relates more specifically to medical applications of radiometers and related devices and methods.

BACKGROUND

There are numerous diseases which can be treated successfully if detected early, but which can cause long term damage if not timely diagnosed and treated. Diseases such as vesicoureteral reflux can cause significant harm to an individual, but are not easily diagnosed without invasive procedures.

In vesicoureteral reflux bladder urine flows back up into the ureters and into the kidneys. The urine can cause kidney infections which can be painful. Moreover, repeated infections can cause long term kidney damage. While vesicoureteral reflux can be treated with medication or by surgical techniques, vesicoureteral reflux is difficult to properly diagnose.

Approximately 2% of all children at any one time have a urinary tract infection. When a child has had more than one kidney infection, it is desirable to determine if the child has vesicoureteral reflux. Two radiologic imaging studies are commonly utilized: voiding cystourethogram (VCUG) and a nuclear cystogram. A VCUG is performed in humans of all ages by first placing a sterile catheter in the patient's urethra and through the catheter instilling radiopaque contrast, such as Cystografin. The kidneys and bladder are observed during a bladder filling and emptying cycle using x-rays. The patient has an initial x-ray film taken, then an anterior-posterior film and then films in each lateral oblique. When voiding is initiated, fluoroscopy is utilized, and spot films are taken to document changes during voiding. This process has been necessary to evaluate bladder anatomy, function, and elimination and to confirm the existence of vesicoureteral reflux. After the first infection it is currently recommended that patients undergo a VCUG and a renal imaging study. However, doctors are sometimes reluctant to order the invasive VCUG until other infections occur. Of the VCUGs performed, approximately one of three patients will have vesicoureteral reflux. The reflux is graded and treatment is assigned on the basis of severity. About three-quarters of the patients are assigned to medical management and are screened with a VCUG each year until their reflux resolves. This averages about three years of waiting before resolution occurs. Patients who undergo surgical correction of their reflux also require a follow-up VCUG to evaluate the success of the procedure. Patients with enuresis either at night or during the day are evaluated with VCUGs on occasion. Since the test is currently invasive, it is withheld until the patients are older or unusual symptoms indicate its necessity. It will be appreciated that the VCUG procedure is uncomfortable and can be traumatic, particularly for children.

Likewise, various other conditions exist in which body fluids, such as urine or blood, improperly flow as a result of disease or dysfunction. For example, gastroesophageal reflux is common in young children. Other conditions involve disruptions in blood flow or myocardial function resulting from narrowing of the aorta, blood clots, or malfunction of the enterohepatic circulation or a portion of this system, e.g., the intestine, liver or gall bladder, or disruptions in flow of cerebrospinal fluid. Diagnosis of such conditions has often required invasive procedures, such as use of catheters or tubes.

Besides the diseases above, body tissues are subject to other abnormalities including cancer, scarring, inflammation and reduced function. One potential effect of the abnormalities includes abnormal tissue abnormally encouraging or restricting thermal spread. Thus, the improper flow of bodily fluids may be a condition that should be treated, or may be a symptom of a disease in need of treatment. Either way, prompt detection of such conditions would be beneficial.

There has been some discussion regarding administering microwave or ultrasound energy through an external energy source to warm a fluid in a target organ or tissue and detecting a warmed fluid distant from the target. (See, e.g., U.S. Pat. No. 7,271,245.) However, blind application of the thermal energy for a predetermined time may cause many problems, such as mis-targeting of the device, over or under heating of the target area, skin burns by mis-placement of the device and/or uncomfortable or damaging heating of the antenna itself against the patient.

There has also been discussion about a flexible microwave antenna array on a flexible circuit board. (See, e.g., U.S. Pat. No. 6,330,479.) However, sensing deep tissue temperature in a noninvasive manner can be difficult, as the emitted energy is small.

As diseases such as vesicoureteral reflux have relied on invasive and traumatic diagnosis procedures, a non-invasive and less traumatic diagnosis method and equipment would be desired. Moreover, a method for diagnosing or treating diseases with thermal energy which does not burn or otherwise discomfort patients would also be desirable.

Other methods of using radiometers and related devices in medical procedures are also desirable, as will be further discussed below.

SUMMARY

Embodiments of improved noninvasive heating and monitoring devices and methods of use are disclosed below. According to some embodiments, one or more microwave antennas are directed at a target organ or tissue, such as the bladder. Signals broadcast by the antenna(s) are used to heat liquid within the targeted tissue or organ (e.g., the bladder, gall bladder, etc.). A temperature sensing device, such as a radiometer, may be directed at the target organ or tissue and its temperature monitored to determine the extent to which heating has occurred at the desired location. The temperature sensing device or a second temperature sensing device may then be directed at a secondary location to detect an abnormal rise (or abnormal lack of rise) in temperature. If the temperature sensed at the secondary location is other than what would be expected in a healthy individual, a reading can be taken which is indicative of a disease or dysfunction. While discussed principally in the context of urine, other body fluids such as blood, bile, cerebrospinal fluid, lymph or other gastric fluids could also be used to diagnose abnormal physical conditions. Similarly, the target organ or tissue may be monitored for an abnormal dissipation of heat as evidence of disease/dysfunction.

In some embodiments, a heating and monitoring device includes an array of microwave elements that direct energy to a focal point or area. These elements may be controlled separately or as a single entity. Likewise, the microwave elements can be used simultaneously or alternatingly to obtain desired heating characteristics.

The elements may be alternately activated such that the focal point is subject to a more consistent thermal energy from alternating microwave elements. However, by alternating the elements, the tissue between the elements and the focal point is subject to only the energy of a single element and at less frequency than the focal point. Thus, the intervening tissue may maintain a lower temperature, while the focal point may be heated to a desired temperature. This may reduce, and hopefully eliminate, discomfort or burns to the surface tissue or intervening tissues, while providing enough energy to heat the focal point to obtain the desired temperature.

Some embodiments provide for a noninvasive method for determining the condition of tissues by administering external energy with an array device to heat a tissue while measuring the temperature changes and heat dissipation of the tissue and comparing to measurements of temperature changes in normal tissues when heated. For example, in some embodiments, an array of microwave elements may include one or more passive elements or sensors that may be used to monitor the temperature of the surface area of the tissue. If the tissues at the surface approach a threshold, the sensors can signal an alarm or may alter the application of energy from the elements. This ensures that the surface temperature does not exceed desired limits and prevents burning or causing discomfort in the individual.

In some embodiments, temperature monitors may be further enabled or enhanced to enable more accurate deep tissue readings. The device may be configured, for example, to disable the active elements (i.e., energy applying elements such as microwave antennas) to reduce any noise produced by the active elements. A passive element or sensor may then take readings between application of energy from the elements to obtain a more accurate temperature measurement due to a decrease in background noise or signals.

The monitors may also be directionally shielded such that the sensor may have increased sensitivity at the desired anatomy, and minimized sensitivity to radiated heat from other tissues. The increased sensitivity and decreased noise may be especially important for deep-tissue or organ observation as the received signal may be as small as −160 dBm.

In some embodiments, the surface area around the microwave elements may be cooled. In some embodiments, the microwave elements may be covered with passive cooling mechanisms, such as water or gel (i.e., a heat sink), to reduce the risk of burns caused by the microwaves. Alternatively, active cooling mechanisms, such as a heat pump, a heat pipe, recirculator, a refrigerated coil, etc., or any other cooling mechanism can be used to keep tissues near the surface cool while deeper tissues are heated.

In other embodiments, monitoring the surface temperature may be used to control how the microwave elements are powered or which of the array elements are active at any particular time. By modulating the power or by selectively activating different elements in the array, the surface temperature and the internal energy deposition at any point may be kept low while still heating the internal target area.

The focal area or another area may be monitored for temperature difference after heating by a detecting mechanism, such as an antenna, disposed in communication with a radiometer. Heat dissipation from the focal area different from normal or control tissue may indicate disease or dysfunction. Similarly, tissue or liquid distant from the focal area may be monitored for unexpected rise, lack of rise or decrease of temperature which may indicate dysfunction or disease, such as vesicoureteral reflux, gastroesophageal reflux, or a number of other diseases.

For example, one or more focused antennas disposed in communication with one or more antennas in communication with radiometers may be positioned on the body of an individual to monitor the temperature change of tissue and/or fluid at a desired depth within the body, such as for detecting fluid temperature in the bladder or some other organ. In some embodiments, focused antennas can be placed such that a change in temperature in the kidneys due to reflux of heated urine from the bladder may also be monitored and thus determined non-invasively. This enables a physician to determine that there is vesicoureteral reflux, gastroesophageal reflux, etc., without having to use a catheter or other invasive procedure and potentially traumatize the individual.

In some embodiments, a radiometer can be used to detect an internal temperature (e.g., the core temperature) of a patient. For example, in some surgeries (e.g., heart surgery), the patient is cooled such that it can be desirable to monitor the core temperature of the patient during the surgery. The radiometer, and potentially additional components, can be configured to receive signals from a desired depth within a patient so as to monitor the patient's core temperature. The term "patient" is not intended to be limiting, and can include individuals who are not necessarily undergoing treatment or other medical procedures. Moreover, although much of the foregoing discussion has focused on human patients, it should be understood that the term "patient" can include any suitable animal subject, such as, for example, pets or other domesticated animals in veterinarian settings.

In some embodiments, a radiometer is positioned within a shielded enclosure that protects sensitive circuitry (e.g., low-noise signal amplification stages) from electromagnetic interference. In further embodiments, the shielded enclosure is coupled with additional shielding material, which may extend about a periphery of the shielded enclosure. The additional shielding material may be configured to rest at or near the skin of a patient, and may conform to the contour of the skin of the patient, so as to shield a volume of the body of a patient from stray electromagnetic (e.g., radiofrequency) radiation.

In other or further embodiments, one or more matching layers may be provided between the radiometer and the skin of the patient. The matching layer(s) can include a dielectric that allows signals to pass through one or more barriers or interfaces (e.g., skin/antenna interface, skin/air/antenna interfaces) more easily or with relatively small attenuation. For example, the matching layer can reduce signal reflections at the one or more interfaces. By way of illustration, in some embodiments where a radiometer is operating as a receiver, one side of a matching layer can be positioned against or near the skin and another side thereof can be positioned against or near an antenna portion of the radiometer so as to provide for enhanced signal propagation from within the body of the patient to the antenna. The matching layer may be used similarly in delivering microwaves from an antenna into the body of the patient.

In other or further embodiments, a layer of metamaterials is provided so as to enhance operation of a radiometer. For example, the metamaterials may be configured to act as a lens for radiofrequency signals, such that the size of the antenna may be reduced.

In other or further embodiments, one or more of the extended shielding material, the matching layer, and the metamaterials may be provided in a modular or disposable unit that can be selectively coupled with a shielded enclosure containing a radiometer. Any suitable configuration for coupling the disposable unit with the shielded enclosure is contemplated. For example, in some embodiments, a disposable unit can include an adhesive layer, which may prevent slippage of the radiometer during use. The adhesive can be double sided, and may be attached to the radiometer at one side thereof and attached to the skin of a patient at the other side thereof. In other or further embodiments, the extended shielded material (e.g., RF shielding material) can extend outwardly beyond the perimeter of the shielded enclosure. The extended shielded material can be washer-like, and may be electrically connected to the radiometer (e.g., may be electrically connected to the ground side of the radiometer). In other or further embodiments, the disposable unit can include a power source, such as one or more batteries, which can be used to power the radiometer. In some embodiments, a pair of connectors can be disposed in or on the reusable portion (e.g., the shielded enclosure) and the disposable unit so as to electrically connect the radiometer with the power source.

These and other features of various embodiments of heating and/or monitoring devices are shown and described in the following figures and related description.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 7 is a cross-sectional view of another embodiment of a radiometer assembly having a removable unit that includes a matching layer, a metamaterials layer, and a shielding extension;

FIG. 8 is a cross-sectional view of another embodiment of a radiometer assembly having a removable unit that includes a matching layer and a coupling device;

FIG. 10 is a cross-sectional view of another embodiment of a radiometer assembly that includes another embodiment of a removable unit.

DETAILED DESCRIPTION

Figure 1:
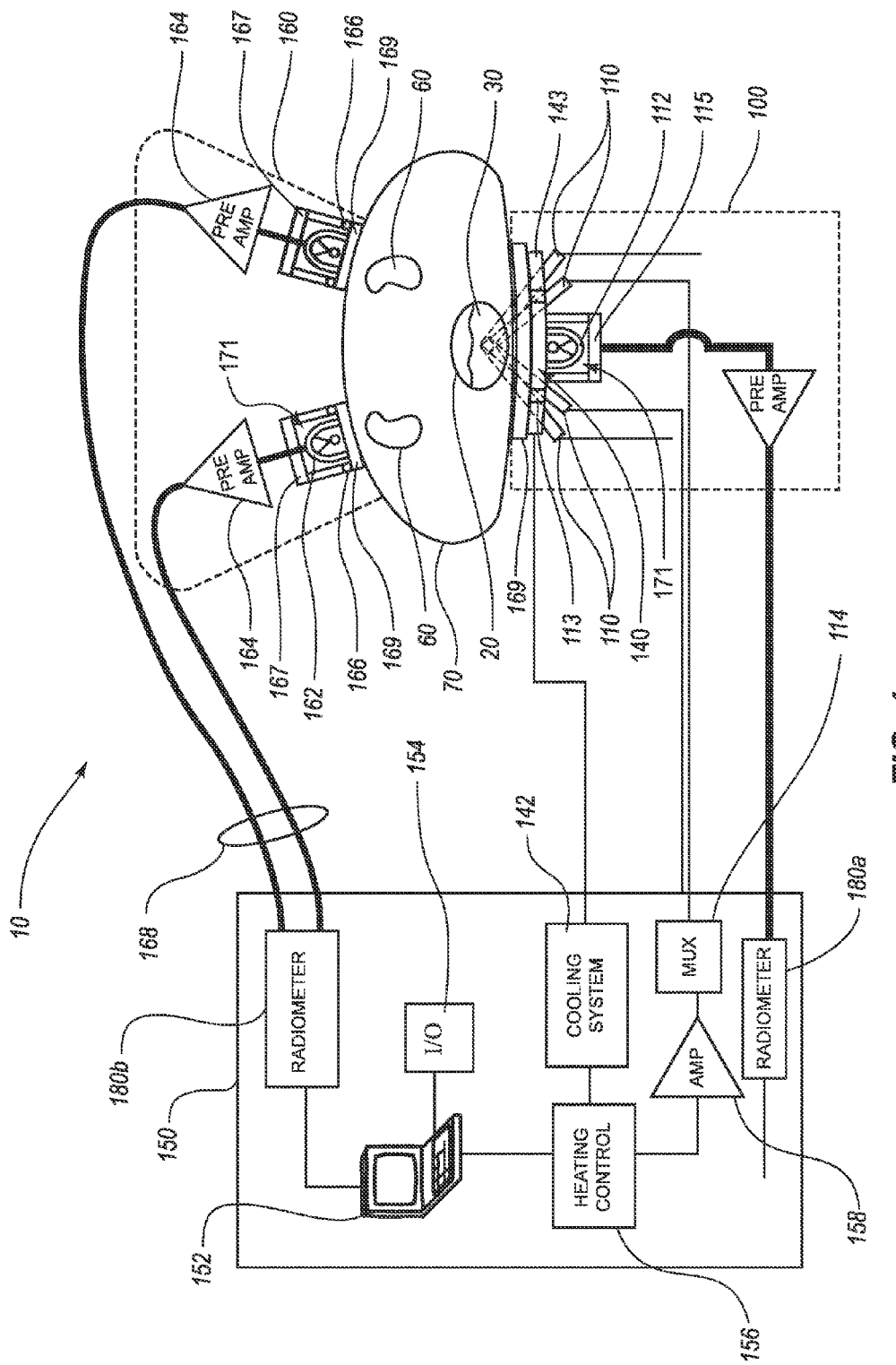
FIG. 1 is a schematic view of an emitted energy heating and/or monitoring system.

Embodiments of heating and/or monitoring devices and associated methods as shown in the accompanying drawings, which include reference numerals referred to below, provide details for understanding and practice by one skilled in the art. The drawings and descriptions are exemplary of various aspects of heating and/or monitoring systems and associated methods and are not intended to narrow the scope of any claims directed thereto.

Turning now specifically to FIG. 1, a schematic representation of non-invasive energy emitting heating and monitoring system 10 is shown. System 10 is shown being used to diagnose a potential abnormal condition of a body 70 by applying heat to a bladder 20 filled with urine 30 to see if the urine flows back to the body's kidneys 60. The system 10 typically includes a heating assembly 100, a control assembly 150, and a monitoring assembly 160.

The heating assembly 100 typically includes microwave elements 110, 112. As will be explained in additional detail below, the microwave elements 110 and/or 112 can be used to heat tissue or fluid and can be used to determine the temperature of those tissues. The microwave elements 110 and 112 may be attached to a substrate 120, and may also include a cooling element or system 140, which is designed to cool tissue at or near the surface while deeper tissue is being heated by the heating assembly 100.

Microwave elements 110 may be directional microwave emitters, commonly known as antennas, and may be configured to supply energy to a specific area in a body 70. For example, microwave elements 110 may be configured to provide microwave energy directionally into a bladder 20 filled with urine 30 so as to heat the urine. Likewise, the elements 110 can be used to heat fluid in other body tissues.

It should be recognized that while much of the discussion about an individual may be related to an adult human, the term "individual" should be read broadly to include children and animals. Likewise, the term "body" can apply to the body of a human or other animal, or of any other suitable subject.

To protect against burning or discomfort, temperature sensors 113 may be provided in the heating assembly 100 for detecting temperature at or near the surface of the individual's body 70. If the sensors 113 detect excess heat, an alarm may be provided, or the heating protocol adjusted to address the situation. Different adjustments are discussed below in additional detail. It will be appreciated that the heating assembly 100 and the monitoring assembly 160 may be a single unit in certain applications.

As the elements 110 are used to heat the target area, it can be desirable to monitor temperature in the target area to prevent overheating. This can be accomplished by the heating assembly using one or more of the elements 110, 112 to detect signals from the target area, which are then passed to a radiometer 180a which indicates the temperature in the target area. While it is possible to use active elements 110 after they have been turned off, in other instances, it can be desirable to use passive element 112 to detect the temperature in conjunction with the radiometer 180a.

Likewise, in certain applications, temperature sensors (e.g., focused antennas) in the monitoring assembly 160 can be used to detect temperature of the target location being heated and/or to detect the temperature in a remote locations, such as the kidneys 60, to ensure that excess heat is not provided, and to gather data used to diagnose an abnormal condition. Thus, for example, focused antenna(s) 162 in the monitoring assembly 160 may collect signals and communicate with one or more radiometers 180b to indicate the temperature at or adjacent kidneys 60.

A control assembly 150 may monitor the system 10 for safety, record the observed results and display the results to the system 10 operator. Thus, the operator may simultaneously monitor the application of heat to (or creation of heat within) one part of the body 70 and detect changes in heat at a second location.

In the heating assembly 100, microwave elements 110 may be placed in an array, and may be arranged and/or spaced apart from each other in the array such that microwave elements 110 provide for a convergence point or area, such that focal area 116 may be affected by the aggregate energy of each of microwave elements 110. Since each of microwave elements 110 may be directional, the energy emitted by microwave elements 110 may travel through body 70 in a generally columnar application. Microwave elements 110 may be arranged in an array in such a way that the convergence of each of microwave elements 110 occurs principally or entirely in the interior space of bladder 20, heating urine 30. This may be accomplished by placing the elements 110 on a flexible substrate 120 or by use of a rigid substrate which can have connections (e.g., pivot attachments) which allow the elements 110 to be angled to adjust for the depth of the target. (For example, a bladder on an overweight adult will be much deeper than a bladder on a thin child.) Alternatively, the heating assembly 100 could be preconfigured for various depths of target tissue, with the physician selecting the assembly which is most appropriate for a particular individual.

In some embodiments, patient anatomy may be consistent enough to allow a holder to naturally direct microwave elements to the target tissue based on placement on the skin. In one embodiment, the physician selects a heating assembly that conforms to the surface of the individual. When placed on the skin using the individual's anatomy as a guide, the elements naturally focus to a target tissue. The holder may include pivot attachments that may have markings that allow the elements to be adjusted based on specific characteristics of the individual, such as height, weight, and/or girth.

Generally, each of the columnar energy emissions heats all tissue or fluids within the columnar area. Thus, focal area 116 will receive an aggregate of the combined energies of the overlapping columnar energy emission areas for that area, increasing the energy absorption and subsequent heating of urine 30 within bladder 20. With four microwave elements 110, as shown in the embodiment illustrated in FIG. 2, the amount of energy applied to the surface of body 70 and other tissues and fluids outside of the targeted focal area 116 may be reduced from that of a single microwave element 110, spreading out the energy over a larger surface area and volume of tissue while not diminishing the energy absorbed in focal area 116. For example, in an array with four microwave elements 110, the skin of body 70 located directly under microwave element 110 will typically receive less energy than would have been required to heat urine 30 with only a single microwave element 110.

In some embodiments, microwave elements 110 may be designed such that each microwave element 110 emits a generally columnar energy emission. In some embodiments, the dimensions of the columnar energy emission may be selected to maximize the profile of focal area 116 while minimizing excess heating of surrounding tissues. The columnar shape or lobes of the radiated energy may be of any configuration desired by a practitioner to provide energy to a focal area 116.

The energy from microwave elements 110 may be additive when supplied to and absorbed by focal area 116. For example, the energy from each of the overlapping focal planes contributes to the energy received by the focal area 116. Adjusting the overlapping focal planes may maximize the energy applied to focal area 116, while minimizing the energy applied to tissues outside of focal area 116. Based on the geometry of the array of microwave elements 110 on heating assembly 100, the energy emitted from the array may be further maximized by adjusting transmission times, direction, frequency, and amplitude of the energy emitted.

For example, in some applications, a first element 110 could emit a high energy emission for a few seconds and then cease. The element 112 could quickly monitor the temperature of the bladder 20 and then a second element could emit a high energy emission for a few seconds, followed by additional monitoring of the temperature of the bladder 20. The process is repeated until the bladder has reached a desired temperature. However, the tissue between the bladder and any given element 110 would heat much less than if a single heating element were used. Moreover, blood passing through non-target tissues would tend to conduct heat away from said tissues, while the liquid in the bladder would tend to retain the heat. Between alternating application of energy and the conductive cooling, the heating in the bladder will be significantly greater than the other tissues.

In other applications, each of the elements 100 (whether it be four or a different number) could be activated in sequence and then the element 112 and radiometer 180a used to check the temperature of the target. By applying energy from multiple locations, the heating of tissue other than the target tissue is reduced, lessening the likelihood of burns or discomfort.

Providing a plurality of different application protocols may be desirable, in some instances, because different tissues or other intervening structures can have different reactions to microwave energy. For example, tissues with higher salt content can absorb more microwave energy than lower salt content tissues. The bladder and muscle tissue have been observed to absorb more energy than does fat tissue. Vascular tissues, such as muscle tissue, appear to cool faster than do non-vascular tissues or static liquids, such as the bladder and its contents.

Taking advantage of this experience, the microwave elements 110 may be activated in different ways depending on factors such as intervening tissue and focal area. For example, when the intervening tissue and structures may be vascular and/or less responsive to microwave energy, a higher power, multiple element simultaneous activation and/or longer duration may be used because of the ability of the tissue to cool and/or absorb less energy. Similarly, if the focal area 116 is within a static liquid with a higher salt content, a higher power, multiple element simultaneous activation and/or longer duration may be used due to heating of the tissue and/or structure.

In other situations it may be advantageous to use lower power, alternating microwave element activation and/or shorter duration. In some cases, it may be advantageous to mix the activation, duration and power settings. For example, in one embodiment, when heating urine, multiple microwave elements may be activated for a short duration with longer periods for conductive cooling.

For example, in one embodiment having four antennas numbered A, B, C and D, the process of heating urine may be the following. Antennas A and C are activated for a short time at high power. The antennas are de-activated and the radiometer readings are examined. If a higher temperature is desired, antennas B and D are activated for a short time at moderate power or high power depending on the sensed temperature. The radiometer readings are then consulted again. If more power is desired, then the process repeats with A and C again.

The process allows the intervening tissue of A and C to cool during the radiometer readings and B and D's activation. Furthermore, it aids in preventing noise during the temperature reading from the passive element 112 and radiometer 180a, as the radiometer may be detecting a small signal that may be on the order of −160 dBm.

In some embodiments, the attitude of each microwave elements 110 relative to each other may be fixed such that the location of the focal area is known based on the physical configuration of heating assembly 100. Similarly, in some embodiments, substrate 120 may be rigid to provide structure to allow fixed relative positioning of microwave elements 110. In other embodiments, rigid microwave elements may be placed on a flexible structure that is carefully placed and may be adhered to the individual. The placement on the body acts as the fixed relative positioning of the microwave elements.

Microwave element 112 may be a passive antenna for monitoring temperatures of portions of body 70. For example, microwave element 112 may be a passive element for measuring the condition, including temperature, specific heat, rate of heat dissipation, etc., of the focus point or focal area. In some embodiments, microwave elements 110 may be used to both emit microwave energy when active, and passively to monitor conditions of tissue, such as temperature, when not emitting energy (although such would be more difficult than using a passive element for such monitoring). In such embodiments, microwave element 112 may not be used. Similarly, in some embodiments, microwave element 112 may be replaced with a focused antenna similar to those in the monitoring system 160 which are in communication radiometer 180.

However, in deeper tissue sensing, it may be more advantageous to have a dedicated sensing antenna as the passive antenna. For example, the temperature signal strength from heated urine may be as small as −160 dBm. Thus, increasing the signal-to-noise ratio may be advantageous. Further discussion regarding using an antenna/element 112 to detect or monitor temperature at a desired depth within a patient is provided below. For example, a radiometer may be used to monitor the core temperature of a patient.

Noise may be reduced by methods including shielding and reducing active interference. The passive antenna/element 112 may be provided with a shield 115 so that detection only occurs in the direction of a target area of the body. Any cable connections between the antenna/element 112 and the receiver, such as radiometer 180a, likewise may be shielded to reduce noise. Active microwave elements 110 may be shielded (i.e., shield 117, FIG. 3) to provide directionality to the focal area while reducing or eliminating other directionality. Active interference may be reduced by causing the active microwave elements 110 to cease transmitting during a window of time that sensing may occur (i.e., during a sensing window). Further active interference may be reduced by causing portions of the control equipment to shut down during a sensing window. In some cases, it may be advantageous to combine the radiometer 180a and passive antenna/element 112 into a single unit that may be placed on the individual. Such a unit may contain one or more of the following: a focused antenna, radiometer, output to a computer, a shielding enclosure, and an analog-to-digital converter.

Impedance matching of the radiometer 180a to the body may also be used to provide a desired signal quality. The impedance may be matched through the fixture 121 (FIG. 3) (i.e., strap or other retention mechanism) to which the antenna is attached. For example, the fixture 121 may use a foam pad to not only conform to the skin's shape, but also impedance match the radiometer to the body. One or more of the passive antenna fixtures may be different than the microwave antenna array fixture, as they may be directed at different anatomy.

In some embodiments, temperature sensors 132 may be used to monitor the surface temperature of body 70 in specific locations, or may be used to monitor the temperature of a cooling system 140. For example, in some embodiments, temperature sensors 132 may be placed adjacent to each microwave element 110, as well as in other areas, to monitor surface temperatures of body 70, and in cooperation with control assembly 150, to reduce the possibility of tissue damage or surface burns. Temperature sensors 132 may be any type of temperature sensor configurable to send electronic signals, such as thermistors, thermocouples, or any other suitable devices.

Control assembly 150 may include PC 152 (or other microcontroller, control system, etc.), heating control 156, amplifier 158 and multiplexer 114 (for controlling heating assembly 100), cooling system controller 142, and radiometers 180a and 180b. I/O devices 154 may be provided for user interaction and input with system 10. Heating control 156, amplifier 158, and multiplexer 114 may be used, along with PC 152, to control the output of microwave elements 110.

In some embodiments, microwave elements 110 may be activated and de-activated in a pattern or sequence to limit potential damage to body 70, while obtaining the desired heating of an internal organ or tissue. Microwave elements 110 may be activated and de-activated simultaneously, or may be selectively activated and de-activated individually and/or concurrently with one or more other microwave elements 110 in a pattern. The power, duration, and sequence of activation of microwave elements may be controlled by heating control 156. The control may further be refined based on measured surface temperatures of body 70, temperatures of cooling device 140, or based on any other desired input or parameter, such as a pre-determined energy output profile or individual physiology and anatomy. Thus, heating control may depend on such factors as body fat content, bladder size/fullness, and the size of the individual.

For example, when heating urine, multiple elements may be activated simultaneously for a short duration at a desired energy level (low, medium or high), followed by an inactive refractory period. Blood flow from vascular tissues, such as muscle, rid the intervening tissue of excess heat. Since the bladder does not have a similar blood flow, the urine will stay heated.

In some embodiments, amplifier 158 may provide microwave energy to microwave elements 110 through multiplexor 114 or from individual amplifiers. In some embodiments, the energy is in the microwave ISM bands. In further embodiments, a frequency range of about 902 MHz to about 928 MHz is used, and in still further embodiments, a frequency of 915 MHz is used. However, other models (e.g., some used outside the U.S.) may use alternate ISM bands. For example, a frequency range of 863 MHz to 870 MHz may also be desirable in some countries, such as those in Europe. The microwave energy supplied by amplifier 158 may be about 100 W at about 915 MHz. Each of microwave emitters 110 may be capable of emitting the entire output of amplifier 158, or some portion thereof. Frequencies and/or or energies other than the illustrative examples just provided are also possible.

In various embodiments, the energy received by a sensor, such as the radiometer 180a or 180b, may be at a frequency that is between about 1 gigahertz and about 4 gigahertz. Without being limited by theory, the energy emitted by the body 70 is believed to correspond to an integral of the heat of all the tissue to the detected depth. The detected depth is believed to depend on the frequency selected. Thus, a measurement at two different frequencies may correspond to a heated volume. The heated volume may then correspond to a temperature at the heated volume. Thus, a multi-frequency radiometer, or two or more radiometers, may be used to detect and/or quantify temperature at a depth in a non-invasive way by comparing first and second energy levels. Another benefit of multi-frequency radiometers is that depth may be adjusted on a per individual basis. In some embodiments, the frequency emitted may more particularly be between about 1.2 to about 1.4 gigahertz.

More generally, one or more complex relationships can relate the depth within the body 70 from which energy is received, the pattern and frequency ranges of the antenna used to detect the energy, and parameters associated with the coupling of the antenna with the body 70 to receive the energy. Theory and/or experimental calibration of one or more of the foregoing factors and their relationships can be used to determine the temperature within the body 70. In certain instances, reception of energy within a wider band of frequencies can yield temperature readings having greater accuracy. In various embodiments, it can be desirable to receive energy within a frequency range of from about 300 megahertz to about 3 gigahertz, or any suitable sub-range thereof (e.g., from one of about 300, about 400, about 500, about 600, about 700, about 800, and about 900 megahertz to one of about 1, about 2, or about 3 gigahertz; from about 1 gigahertz to about 2 gigahertz; from about 1 gigahertz to about 3 gigahertz; or from about 2 gigahertz to about 3 gigahertz). A variety of antennas and coupling devices and techniques are discussed further below.

Measurements obtained via such sensors may then be compared to an actual, normalized, or expected energy level. The normalization may be based on anatomical data. In one embodiment, the examined depth may be between 2 cm and 7 cm. In one embodiment, the measured levels are presented by an image. The image may be based on actual values or calculated values, such as a delta between actual and expected values. In some cases, quantifying the data may require integration to determine an aggregate of energy change.

In some embodiments, a target of total energy supplied by system 10 to body 70 may be about 5 W to 60 W over about 5-20 min. The amount of energy emitted should be sufficient to heat the targeted body portion to a desired temperature, such as raising the temperature of urine 30 a measurable amount over body temperature. The target temperature may be sufficient such that the heated urine may be detected in the kidneys during a reflux event, but not so hot as to damage tissues or cause significant discomfort. Heating assembly 110 may be connected to control assembly through connector 114.

In some embodiments, cooling system 142, along with cooling element 140, may be used to cool the surface of body 70 at or near where heating assembly 100 supplies energy to body 70. In one embodiment, cooling system 142 may circulate and monitor cooling fluid through cooling element 140. The cooling system 142 may also alternatively actively remove heat from the area using a heat sink, heat pump, heat pipe, or other similar devices alone or in combination, as represented by structure 143. Cooling system 142 may provide signals to heating controller 156, indicating the temperature and status of the cooling system and/or surface of body 70, such that the system may maintain a safe operation. In one embodiment, the cooling system is controlled based on signals from the controller.

In some embodiments, system 10 may not have cooling system 142, but only cooling element 140. Cooling element 140 may be a cooling gel, water, or other cooling medium or device. In some embodiments, cooling element 140 may be configured to be replaced intermittently as cooling element is heated by energy emitted from microwave elements 110. In some embodiments, cooling element 140 may be fixedly coupled to substrate 120. Cooling element 140 may be configured to circulate a cooling medium, such as water, or may house, or be formed from a cooling medium, such as a cooling gel.

In one embodiment, a heat sink and heat pipe structure (collectively 143) is embedded in a flexible and disposable fixture. The heat sink collects heat from the body surface and/or the microwave antenna elements. The heat pipe then wicks away the heat from the heat sink. The heat sink and/or heat pipe may have internal temperature sensors to report the current temperature of the system. If used in conjunction with temperature sensors on the skin, the system may be able to determine the effectiveness of the cooling system. Effectiveness of the cooling system may also be a lead indicator of blockages or stoppages of active or passive portions of the system. These problems may include heat sink fin buildup, clogged heat pipes, or lack of sufficient cooling medium (air or water).

Monitoring assembly 160 may include one or more focused antenna 162. Each of focused antennas 162 may have one or more corresponding signal conditioners including preamps 164 and filters and positioner 166. Monitoring assembly 160 may have shielding 167 to shield the focused antennas 162 from the control assembly 150 and/or other sources of stray electromagnetic radiation. The shielding may be used to avoid interference and to allow proper calibration and detection by each focused antenna 162. The shielding 167 may be a fabric, mesh, or any other suitable material. Important shielding may include conductive shielding from the active antennas and the individual's skin, thus preventing potentially substantial causes of ambient noise. The shielding 167 may be constructed as part of a disposable fixture, through materials such as conductive foam. Further discussion of arrangements and constructions that are suitable for the shielding 167 is provided below.

Focused antenna 162 may be positioned to detect changes of temperatures in the body, such as kidneys 60. In some embodiments, multiple antennas 162 may be used to detect temperatures in various locations in each kidney 60, or of each kidney 60, independent of each other. Monitoring assembly 160 may be connected to control assembly 150 by connector 168. Similarly, a focused antenna 162 may be used to monitor the temperature of urine 30 in bladder 20, and may be positioned with or may be incorporated into heating assembly 100. In some embodiments, the desired depth of measurement within the tissue may be adjusted based on physiological and biometric data, as well as frequency and intensity adjustments.

The frequency may be adjusted based on several different factors. The adjustment may be normalized on typical anatomy measurements. In some embodiments, the adjustment is based on inferred or measured data from other imaging data, such as an ultrasound, MRI, or from prior baseline measurements. In other embodiments, the entire area may be imaged by varying the sensor's detected frequency range.

Radiometer 180b may be provided in control assembly 150, or in monitoring assembly 160, to receive input from focused antennas 162 and provide coherent data to PC 152 corresponding to the input from focused antennas 162. In some embodiments, the radiometer may be located in monitoring assembly 160, such as within the shielding 167 of monitoring assembly 160.

Positioner 166 may be configured to work in conjunction with a fixture of focused antenna 162 to allow a practitioner to direct the focused antenna 162 to detect temperature in a desired location within body 70. A practitioner may locate one or more anatomical features to facilitate desired positioning of focused antenna 162 over tissue, internal body portions and/or fluids at a depth to be monitored, such as a bladder with urine, or a kidney. In some embodiments, a focused antenna may be placed to detect both the temperature of urine in a bladder, and a second focused antenna may be placed to detect the temperature of fluids in a kidney. In some embodiments, the anatomical feature may be detected using ultrasound to ensure proper placement of focused antenna 162. Positioner 166 may then be used to hold focused antenna in place, and may be adjusted as desired. The described methods of positioning of focused antenna 162 may also be used to position heating assembly 100.

Steps to use the device may include: Locating an anatomical feature associated with a first desired internal body portion; positioning a first device based on the locating the anatomical feature, wherein the first device is configured to alter a condition of the first internal body portion; positioning a second device on the individual, wherein the second device is configured to monitor the condition of a second internal body portion; and applying microwave energy from the first device to the individual, the energy being configured to increase the temperature of the first internal body portion without injuring the individual. Further steps may include: monitoring the condition of the second internal body portion; locating a second anatomical feature associated with the second desired internal body portion, wherein the positioning of the second device is based on locating an anatomical features associated with the second desired internal body portion; or using an ultrasound device to locate the anatomical feature.

In some embodiments, positioner 166 may be disposable. For example, a disposable contact member with positioners 166 may be provided to directly contact body 70, allowing monitoring assembly 160 to be attached in the appropriate location relative to body 70, while allowing for the disposable contact member to be thrown away after each use, or when soiled by a individual being treated with system 10. For example, positioner 166 may include an adhesive portion for temporarily affixing positioner 166 to an individual being treated.

In some embodiments, positioner 166 may include an impedance matching element 169 placed between focused antenna 162 and the individual being treated. The impedance matching element 169 may be selected based on measured biological data from the individual to allow focused antenna to be tuned for each individual being treated. The impedance matching element 169 may be formed from plastic, or other suitable material, and may be physically designed to provide a desired impedance matching effect, such as thickness, density, dielectric constant, etc. In some embodiments, the impedance matching element may be formed such that it may be affixed to the individual being treated, diagnosed, or otherwise acted on or observed, and may be used as a positioning aid to help place focused antenna 162 in correct position relative to the physiology of the individual being treated.

In another embodiment, a fixture 121 may be adhesively applied to the body 70. With reasonable placement, normal contours of the body may direct the focused antenna 162 to the correct anatomic regions. In some embodiments, the impedance matching element 169 may comprise a conductive foam. In some instances, at least a portion of the impedance matching element 169 may be used around the focused antenna 162 to shield the focused antenna 162 from noise. A dielectric foam or other suitable impedance matching element may be applied between the antenna and the body to aid in a predictable electrical pathway to the desired target area.

The fixture 121 (FIG. 3) may be configured with a receptacle 171 to accept and release the focused antenna 162 or an assembly containing the focused antenna, such as a combination of antenna and radiometer. In other or further embodiments, the fixture 121 may have receptacle 171 for the passive antenna 112 (which can function as a focused antenna). As the antenna and/or assembly may be expensive, reuse of the assembly may be cost effective. Thus, the disposable portion of the fixture 121 may include the receptacle that directs the focused antenna 162 or passive antenna 112 to the proper target area, while providing shielding. Further embodiments of removable and/or disposable units or fixtures are discussed below.

The rate and magnitude of thermal change may be compared to expected data. The differences may indicate a disease and/or diagnosis, as well as a measurement of severity. Further, the data may indicate or provide a factor of indication in the amount and duration of fluid migration between bladder and kidney. Thus, with normalized data, the system may include a temperature trigger that may automate a portion of the diagnosis and/or determination of severity.

Measurements by the system of thermal changes may be converted to graphs or other visualizations of the measured data set, including color real-time manipulable 3-dimensional images. The visualizations may grant an operator a quicker understanding of the data. As discussed above, the image data may be based in the integral of the temperature in the direction of the temperature sensor (such as a radiometer). More resolution may be obtained by overlapping sensor detection areas, especially with a different direction. In fact, the image may aid the operator's use and diagnosis in real-time. In some embodiments, the image may be displayed on I/O device 154, as I/O device 154 may be one or more of a monitor, touch screen monitor, or other data entry device keyboard, mouse, or any other I/O device desirable for use with system 10.

In some embodiments, heating controller 156 may be used to control a safety turn-off based on temperatures monitored in or on body 70. Algorithms may be used to limit energy output based on the size and age of the individual, inflated size of the bladder, thickness of muscle and intervening tissue, temperature sensors in the cooling apparatus, any temperature sensors in the bladder, and temperature sensors on the skin. For example, if input from temperature sensors 132, passive microwave element 112, focused antennas 162, or other input indicates the possibility or likelihood of injury to body 70 or an anomalous reading, heating controller 156 may shut down the procedure to avoid injury to body 70. Similarly, temperature inputs may be constantly monitored and the output at microwave elements 110 adjusted accordingly to optimize the heating rate and avoid injury or unwanted tissue damage, according to anatomy. Such adjustment, safety shutdown, and monitoring may be done automatically by control assembly 150. Adjustments may include: selectively cycling which portion of the focused array emits energy; altering the duration of time the focused array emits energy; altering the period at which at least a portion of the focused array emits energy tuning off the focused array, etc., such that an optimum energy may be emitted without damaging tissue.

In one embodiment, the heating assembly 100 and the monitoring assembly 160 may be wirelessly coupled to the control assembly 150. The wireless coupling may allow the individual more comfort and/or freedom of movement. In some procedures, the individual may be required to urinate the heated liquid. With wireless coupling, the individual may be able to use a normal restroom while being diagnosed.

With remote monitoring, the system may require more hardware that is respectful of the equipment. For instance, the wireless communication may cease during the detection phase of a radiometer to reduce interference. Thus, the system may have local storage to store and forward the results after the measurements. Procedures may also have different power requirements. Thus a lower power procedure may use a small portable power supply, such as a battery or fuel cell, that may strap on the individual. Higher power procedures may require a power supply that is separately wheeled by the individual or an attendant.

Figure 2:
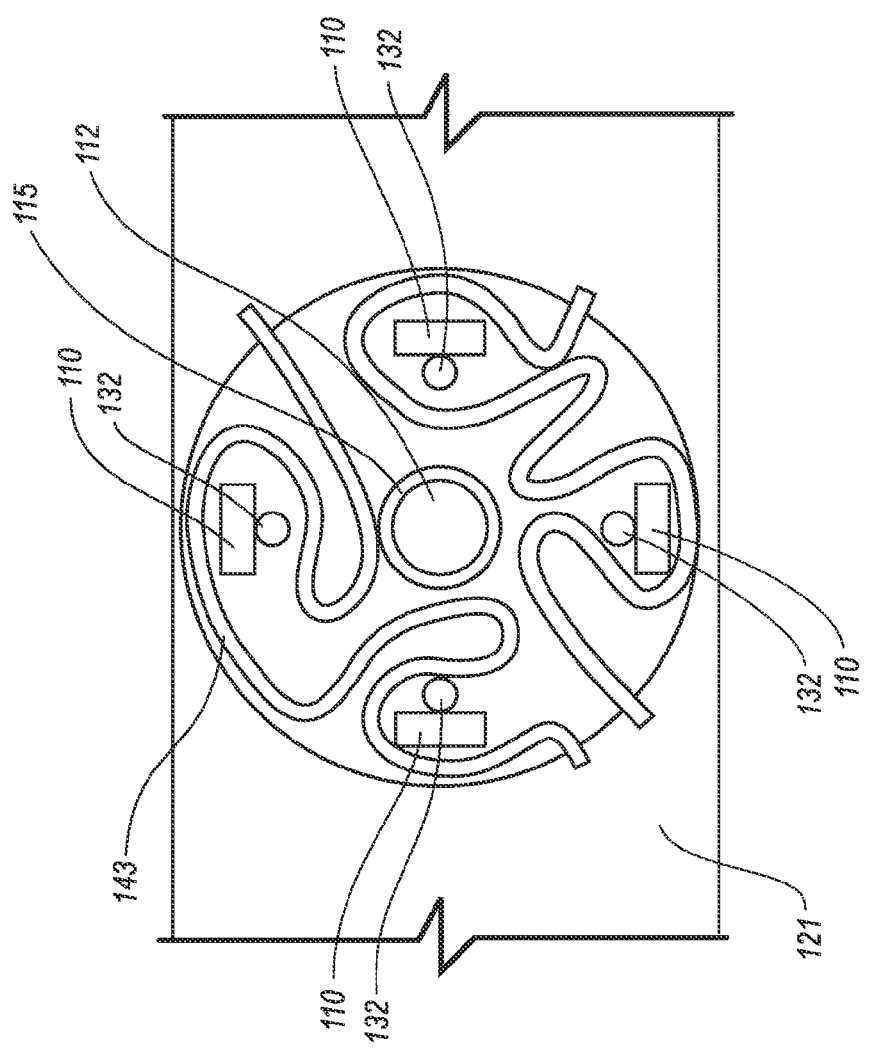
FIG. 2 is a schematic view of an emitted energy heating and/or monitoring device.

Turning now to FIG. 2, a schematic view of an emitted energy heating and monitoring device is shown. The array may have two or more of microwave elements 110. FIG. 2 illustrates four microwave elements 110. It will be appreciated that as many microwave elements 110 as desired may be used in the array on heating assembly 100. In some embodiments, microwave elements 110 may be lobes of a single microwave antenna, generating separate energy emissions from each lobe such that the lobes work in a manner similar to distinct microwave elements 110 as described below.

The heating assembly may include rigid microwave elements 110 on a flexible, disposable fixture 121 such as a band, strap, or other retention mechanism. The fixture 121 may contain or use a layer, such as a dielectric foam, allowing the microwave antenna a more predictable electrical pathway to the focal area. The system may also be shielded, which can prevent stray electromagnetic radiation from interfering with operation of the microwave elements 110 and/or can prevent the scattering of microwaves to the back or side of the assembly. This shielding may be accomplished through a backplane, more conductive foam, or other shielding methods.

Figure 3:
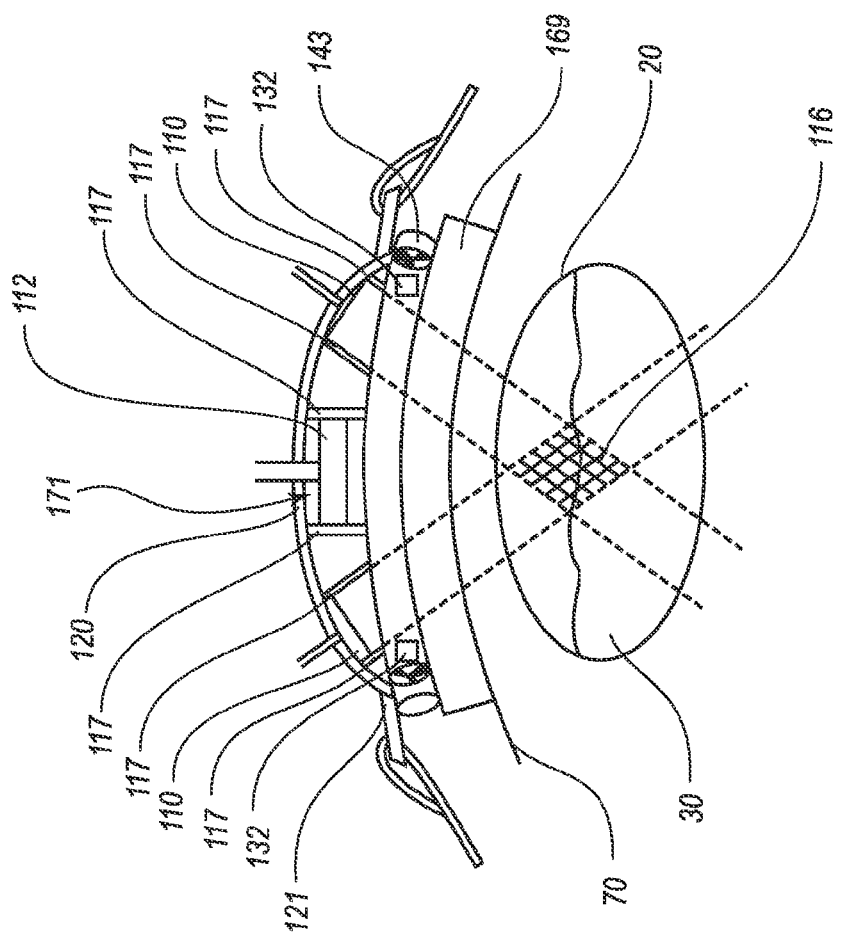
FIG. 3 is a cross sectional view of an emitted energy heating and/or monitoring device in use on an individual.

Turning now to FIG. 3, a cross sectional view of an emitted energy heating and monitoring device 100*a* in use on an individual is shown. Individual microwave antennas 110 may be directed to a focal area 116, such as urine in an individual's bladder. A cooling element 140 may be used to reduce the temperature of the skin as raised by the microwave antennas. A passive antenna 112 (or focused antenna) may be used to monitor the temperature at the focal area 116 and/or a target area for diagnosis.

Thus, the heating and monitoring device 100*a* may form the heating assembly 100 and may be used in conjunction with the monitoring assembly 160, or may be used for both functions in appropriate circumstances, i.e., determining temperature change in a relatively small area.

Although system 10 has been described with microwave elements 110, other heating methods may be provided and used with other portions of system 10. Similarly, the components of system 10 may be provided in any number of configurations, and not necessarily in the particular configurations and locations illustrated in the figures. For example, multiplexor 114 may be located on substrate 120 of heating assembly 100, or PC 152 may be remote from the rest of system 10, being connected wirelessly to other components of system 10. Other configurations and uses, either individually or with one or more other components taught in the figures, are contemplated by this application.

While much of the foregoing disclosure focuses on vesicoureteral reflux, there are numerous other suitable scenarios and contexts in which the devices and methods can be used.

For example, systems and methods of the present disclosure can be used with the nervous system. There is not a current imaging method that adequately shows flow of the cerebral spinal fluid through the aqueducts to and from the spinal column. Current studies simply show dilatation of obstructed chambers. Warming either the spine or the head and measuring the temperature in the opposite end (or some other location) of the nervous system, using systems and methods disclosed herein, would easily show the migration of the warm cerebral spinal fluid through its proper ductal network. This flow could be timed to know how rapid this occurs and whether any abnormalities exist.

Likewise, systems and methods of the present disclosure could be used in the dental field. For example, a patient could drink a warm liquid or a cold liquid and it could be measured how rapidly the teeth return to a normal temperature, indicating good blood flow and viability of the teeth. Sensitivity to hot or cold is a common problem and it can be difficult to determine exactly which tooth is causing the problem. Certain systems and methods of the present disclosure, with their ability to determine actual temperatures, may be very helpful in determining the underlying condition.

Likewise, certain embodiments could be used in the pulmonary field. Anticipated benefits for imaging the pulmonary tree may be significant. Currently there are few diagnostic studies to determine ventilatory patterns deep within the bronchial tree and the alveoli. The patient could be asked to breathe warm or cold air and the systems and methods of the present disclosure could measure temperature changes throughout the lung fields, determining which areas were easily ventilated and watching their return to normal.

Certain systems and methods of the present disclosure could be used as a way to watch the lung disease processes resolve. Once a patient has breathed warm or cold air, certain systems and methods of the present disclosure should be able to observe the normal blood vessels that do not change with the ventilation temperature to determine perfusion in the lungs, and ought to be an alternative method to evaluate ventilation and perfusion defects.

Certain systems and methods of the present disclosure could also be used in the cardiovascular context. For example, an individual could have the heart warmed and then measurements of peripheral blood flow to any of the following arteries: carotid artery, femoral artery, brachial artery descending aorta, etc. The systems and methods could be used to measure peripheral vascular blood flow. By knowing how rapidly the heart was warmed, a mathematical calculation of cardiac output could be performed.

As the resolution of certain systems and methods improves, it may be possible that the coronary vessels could be seen distinctly from the heart chambers themselves, allowing imaging that is currently only available by intravascular catheterizations. Conversely, if a peripheral area, such as a femoral area was warm, one could watch and calculate venous return to the heart, including cardiac output.

Certain systems and methods of the present disclosure could be used if the lung fields were warmed, either the right side or the left side, or both sides at once, to observe the vascular tree of the lungs, both pulmonary artery and pulmonary venous systems could be well-delineated.

If an IV was in place, an injection of cold bolus of fluid of known amount could be injected and certain systems and methods disclosed herein could be used to measure the temperature and with thermodilution calculations the cardiac output could be determined accurately.

Certain systems and methods of the present disclosure could be used in the genitourinary system (besides vesicoureteral reflux). For example, if the kidney were warm, the urine flowing to the bladder could be seen and measured, thereby alleviating the need for an intravenous pyelogram (WP) and at much diminished expense from a CT scan. Warmed bladder urine could be observed during the voiding process and perhaps eliminate the need for voiding cystoureterograms in non-refluxing patients.

On occasions, renal cysts are difficult to delineate from a diverticula of the collecting system, which does have a communication with the collecting system. If the fluid pocket was warm and the temperature changes, one could tell it was a diverticulum with the communication to the kidney and if the temperature simply diffused through the kidney, one would know this is a cyst without fluid communication.

Regarding GI imaging, swallowing warm or cold fluid could be used in conjunction with certain systems and methods of the present disclosure, as the temperature monitoring devices may be used to evaluate esophagus transit and stomach transit times. If the stomach were warm, observation of the esophagus would determine whether there was gastroesophageal reflux. If the stomach were warmed or if warm or cold fluids were swallowed, the intestinal transit time may be calculable with the systems and methods of the present disclosure.

Likewise, the traditional barium enema to study the large intestine may still require the catheter and fluid to be placed, but the temperature of the fluid could be adjusted so that the systems and methods of the present disclosure could be the imaging modality of choice so that no ionizing radiation is required.

Similarly, the flow of bile from the gallbladder through the bile duct could be imaged by warming the gallbladder and watching the warm bile go down the duct into the duodenum. Certain systems and methods of the present disclosure could render such monitoring relatively easy and noninvasive.

In obstetrics and gynecology, the hysterosalpingogram study to determine patency of the fallopian tubes could be done with a cold solution and imaged with the systems and methods of the present disclosure so that no ionizing radiation would be necessary, especially in the area of the gonads, which can be damaging.

Likewise, during pregnancy, the amniotic fluid could be warmed and the turn over time of the amniotic fluid could be measured, fetal swallowing could be observed, and fetal urination would be visible.

In orthopedics, joint spaces have fluid and the fluid could be warmed and observed for even distribution throughout the joint space. This may be a desirable tool for physical therapy for measuring how deep the tissues are being heated and how rapidly the damaged tissue is responding and returning to normal blood flow.

Regarding solid organs, or tissues, scar tissues should warm much differently than normal surrounding tissue because of missed blood flow, and over time it would be anticipated that the scar tissue would cool more slowly since there is less blood flow to take the warmth away from the scar. This would help physicians determine whether there was scar tissue or inflammation.

Within inflamed tissue there should be increased blood flow, which should have a different warming characteristic of scar tissue, and with the increased blood flow it would be expected that the inflamed tissue would cool faster as the increased blood flow would take the temperature away.

From the foregoing discussion, it will be appreciated that in various embodiments, the system 10 can be configured primarily or exclusively for monitoring temperatures of a body of a patient. For example, one or more microwave elements or antennas 112 of the heating assembly 100, and/or one or more antennas 162 of the monitoring assembly 160, may be used to determine and/or monitor a core temperature of a patient. In various embodiments, the one or more antennas 112, 162 may be configured to receive signals from a relatively deep location within a patient, such as from a depth that is within a range of from about 0.5 to about 6, from about 2 to about 6, from about 3 to about 4 centimeters below the surface of the skin, or is no less than about 0.5, 1.0, 1.5, 2.0, or 3.0 centimeters below the surface of the skin. In some embodiments, the system 10 may be used primarily for temperature monitoring, and thus may include a monitoring assembly 160 but not a heating assembly 100.

In some embodiments, the core temperature of a patient is monitored while a separate medical procedure, such as a surgery, is conducted. For example, in some instances, a patient may be cooled during open-heart surgery, such that it may be desirable to maintain an accurate reading of a deep tissue or core temperature of the patient during the surgery. Embodiments of the system 10, which may include a monitoring assembly 160, can obtain such readings, and may advantageously obtain these readings noninvasively. In some embodiments, an antenna 162 can be placed at or near the surface of the skin of the patient, such as on the forehead, abdomen, or at any other suitable location for monitoring the core temperature.

In monitoring the temperature within a patient, it can be desirable for the extremely sensitive low-noise amplifier stages of certain embodiments to be shielded from external electromagnetic (e.g., radiofrequency (RF)) sources. By way of illustration, the blackbody radiation emitted from a source within the human body is often measured in picowatts, whereas manmade noise from wireless devices can be thousands of times more powerful than this. Accordingly, the pre-amplifiers 164 that are shown at an exterior of the shielded enclosures 115 in FIG. 1, in some arrangements, may instead be positioned within the shielded enclosures 115. Additionally, although the radiometers 180a, 180b are shown at an exterior of the shielded enclosures 115 in FIG. 1, the radiometers 180a, 180b may instead be positioned at an interior of the shielded enclosures 115.

Any suitable combination of the following embodiments, and features thereof, may be used with the systems that have previously been discussed. Similarly, any suitable combination of any of the embodiments discussed herein, and features thereof, is possible.

Figure 4B:
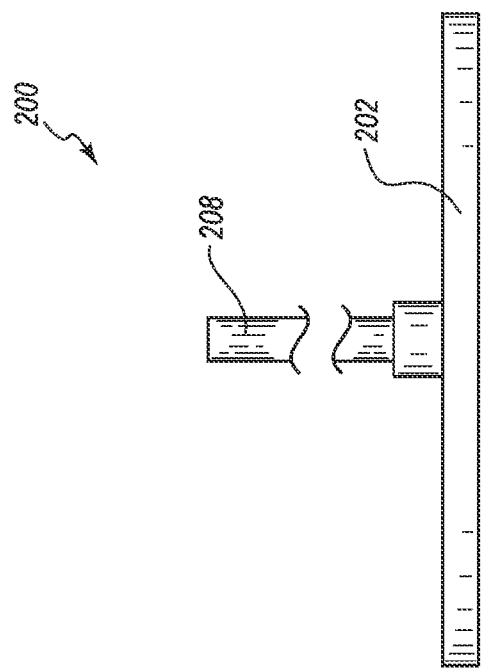
FIG. 4B is a side elevation view of the antenna assembly of FIG. 4A.
Figure 4A:
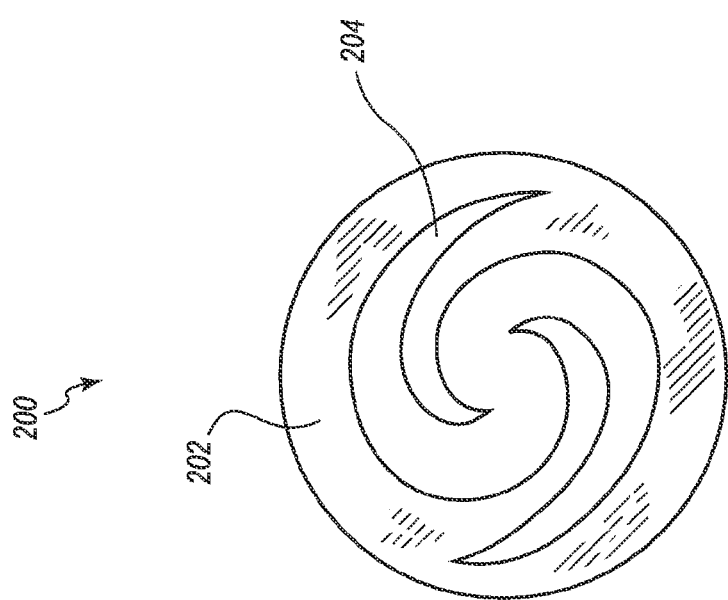
FIG. 4A is a bottom plan view of an embodiment of an antenna assembly configured for use with a radiometer.

FIGS. 4A and 4B illustrate different views of an embodiment of an antenna assembly 200 that can be used with the systems discussed above. For example, the antenna assembly 200 can be used with the radiometer 180b to gather electromagnetic radiation that emanates from within a patient so as to monitor an internal temperature (e.g., the core temperature) of the patient. The antenna assembly 200 may also, or alternatively, be used with the radiometer 180a to deliver microwave energy to the patient in any suitable procedure, such as those discussed above.

The antenna assembly 200 can include a substrate 202 and a microwave element or antenna 204. The antenna 204 can define any suitable shape or arrangement, and can be configured to receive electromagnetic signals from a patient (e.g., microwave or other signals). In the illustrated embodiment, the antenna 204 defines two spiraled branches. Different shapes (e.g., turn shapes) and sizes (e.g., radii), and/or more or fewer branches are possible. Such features can be optimized to receive signals that are from a desired depth within a patient and/or that are within a desired frequency bandwidth. In the illustrated embodiment, the antenna 204 is rigid or substantially inflexible, and is substantially planar. Any other suitable arrangement is also contemplated.

In other embodiments, the antenna 204 may be flexible. In certain of such embodiments, the antenna 204 can conform to the contour of the portion of the body 70 to which energy is delivered by the antenna or from which the antenna receives energy. A flexible antenna 204 likewise may provide tighter RF coupling, as compared with inflexible counterparts, which can reduce RF energy leakage or interference. This may be particularly true where the antenna 204 is used as a receiver and the RF interference is from external sources. The pattern of the antenna 204 (e.g., shape, size, and/or orientation of arms or branches) can be designed to accommodate or cooperate with the curvature of the portion of the body 70 with which the antenna 204 is expected to be coupled.

Any suitable electrical connection can be made between the antenna 204 and a radiometer (e.g., either of the radiometers 180a, 180b). For example, in some embodiments, the antenna assembly 200 can include a conductive post 208 by which electrical and/or mechanical coupling can be achieved between the antenna 204 and the radiometer.

Figure 5:
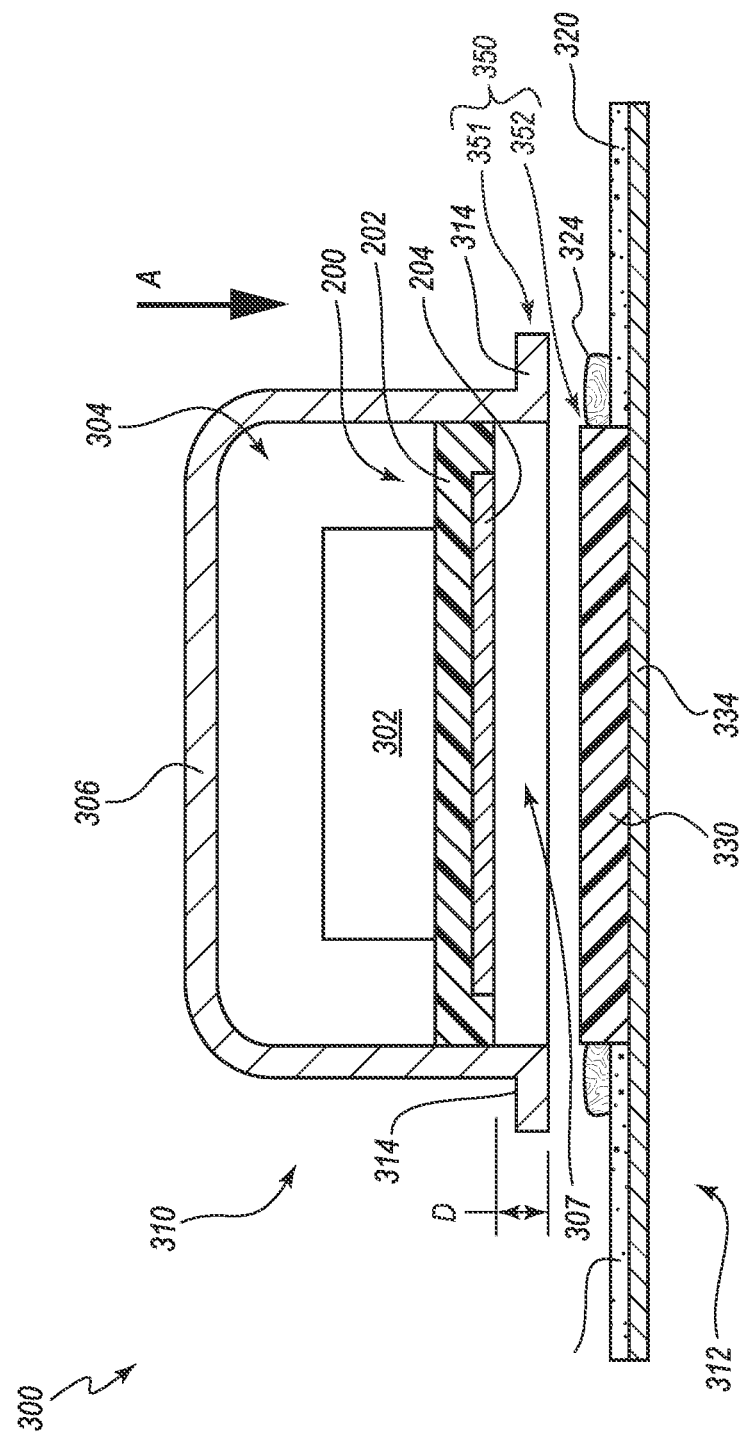
FIG. 5 is a cross-sectional view of an embodiment of a radiometer assembly having a removable unit that includes a matching layer and a shielding extension.

FIG. 5 illustrates an embodiment of a radiometer assembly 300 that includes a radiometer 302 positioned within a cavity 304 of a case, cup, enclosure, or shield 306. The radiometer 302 can be the same as or similar to the radiometers 180a, 180b discussed above, and the shield 306 can be the same as or similar to the shielding 167 discussed above. For example, the radiometer 302 can be configured to receive signals from the antenna 204 and can be used to sense or otherwise obtain a temperature reading based on the signals. The shield 306 can encompass at least a portion of the radiometer 302 so as to shield the radiometer 302 from stray electromagnetic radiation at an exterior of the patient. The shield 306 can comprise any suitable conductive material or materials, such as a metal (e.g., copper), and may be formed in any suitable manner (e.g., stamped, deep drawn). In the illustrated embodiment, the shield 306 and other components of the assembly 300 are substantially cylindrical, or circularly symmetrical about a vertical axis, but other suitable arrangements are also possible (e.g., rectangular). The shield 306 can define an opening 307 at a lower end thereof through which electromagnetic energy can enter or exit the shield 306.

The radiometer 302, which is shown schematically in FIG. 5, may be electrically coupled with a control assembly 150 (see FIG. 1) in any suitable manner. For example, in some embodiments, shielded electrical leads (not shown) may extend through a sidewall of the shield 306 from the radiometer 302 for coupling with the control assembly 150.

The radiometer 302 may be coupled with an antenna assembly 200 in any suitable manner. The substrate 202 and the antenna 204 are shown in cross-section. In some embodiments, the tips of the branches of the antenna 204 are spaced from the inner wall of the shield 306, as shown. The antenna assembly 200 can be recessed within the shield 306 by a depth D, as discussed further below.

In certain embodiments, it can be desirable for at least a portion of the radiometer assembly 300 to be reusable. For example, the radiometer 302, the shield 306, and/or the antenna assembly 200 can be relatively expensive, such that it can be economically desirable to repeatedly use these portions of the radiometer assembly 300 with a series of patients. In the illustrated embodiment, these components are assembled together as a reusable unit 310. The reusable unit 310 can be configured to be selectively coupled with a modular, removable, or disposable unit 312. Any suitable coupling arrangement is possible for the reusable and disposable units 310, 312. For example, in various embodiments, quick and/or easy attach-and-release mechanisms may be used, such as snap-fit, magnetic, hook-and-pile, temporary adhesive, or other suitable fastening arrangements. In FIG. 5, the assembly 300 is shown in a disassembled state, with the reusable unit 310 and the disposable unit 312 being advanced toward each other into a coupled state (as depicted by the arrow A).

In some embodiments, different combinations of the components are included in the reusable and disposable units 310, 312. For example, in some embodiments, the antenna assembly 200 may be part of the disposable unit 312, rather than the reusable unit 310 as shown, and this component may be selectively coupled with the radiometer 302. In other embodiments, such as those similar to the embodiment of FIG. 1, the radiometer may be positioned at an exterior of the shield 306. Accordingly, other components may be included in the reusable unit 310, such as pre-amplification circuitry. In some embodiments, one or more components of the reusable unit 310 are permanently attached to each other so as to form a cohesive unit, whereas in other embodiments, one or more components may be selectively attachable to other components of the reusable unit 310. For example, in some embodiments, the antenna 204 may be selectively attachable to and detachable from the radiometer 302, and in other or further embodiments, the radiometer 302 may be attachable to and detachable from the shield 306.

The disposable unit 312 can be configured for interfacing with a patient while distancing the reusable unit 310 from the patient. For example, the disposable unit 312 can be configured to couple with the skin of a patient, and further, can be configured to prevent direct contact between the reusable unit 310 and the skin of the patient. As a result, in some instances, the reusable unit 310 may be used repeatedly with little or no disinfection or sterilization thereof between uses.

The disposable unit 312 can be discarded after a single use, which can make the overall assembly 300 more economical. For example, in some embodiments, the disposable unit 312 includes less expensive components than those contained in the reusable unit 310.

In the illustrated embodiment, the disposable unit includes an extended shield, shielding margin, or shield extension 320 that is configured to extend outwardly from the primary shield 306 when the radiometer assembly 300 is in an assembled state. The shield extension 320 can form a rim about at least a portion of the shield 306. For example, the shield extension 320 can extend about an entirety of the shield 306 and can project outwardly from the shield 306. The shield extension 320 thus can provide electrical (e.g., RF) shielding that extends beyond the edges of a primary shield 306, such that stray electromagnetic radiation from outside of the patient may not interfere with electromagnetic radiation generated within the patient. Such a shield extension 320 may desirably be flexible so as to maintain contact with the skin of a patient, and may be comfortable for the patient. The shield extension 320 may comprise an electrically shielding fabric, foil, or other suitable material that surrounds or encompasses the shielding enclosure, and may readily conform to the skin surface of a patient. In various embodiments, the shield extension 320 can comprise, for example, conductive cloth, copper mesh, and/or copper foil.

The shield extension 320 can desirably be configured to form a sound or effective electrical contact with the shield 306. In some embodiments, a strip of any suitable conducting paste 324 may be positioned along an inner region of the shield extension 320 at which a lower flange 314 of the shield 306 connects to the shield extension 320. The conducting paste 324 may create or enhance a physical and/or electrical connection between the shield 306 and the shield extension 320. In other or further embodiments, the shield extension 320 can resemble a washer and can be electrically connected to the radiometer 302. For example, the shield extension 320 can be electrically connected to a ground side of the radiometer 302.

In some embodiments, the disposable unit 312 includes one or more matching elements 330, which can be positioned between the skin of a patient and the antenna 204. The matching element 330 can be configured to provide impedance matching or RF matching that can assist with a desired functioning of the radiometer 302 when the assembly 300 is used with human or other animal subjects. Such subjects can vary from one to another due to such factors as different amounts of skin, fat, and muscle thickness. Accordingly, different matching elements 330 may be used for patients of differing anatomies. In various embodiments, the matching element 330 may have a thickness that is within a range of from about 0.1 mm to about 2.0 mm, that is no greater than about 0.1, 0.2, 0.3, 0.4, 0.5, 1.0, 1.5, or 2.0 mm, or that is no less than about 0.1, 0.2, 0.3, 0.4, 0.5, 1.0, 1.5, or 2.0 mm. In other or further embodiments, the matching element 330 may have a dielectric constant that is within a range of from about 5 to about 50, is no less than about 5, 10, 15, 20, 30, 40, or 50, or is no greater than about 5, 10, 15, 20, 30, 40, or 50. In various embodiments, the matching element 330 may be particularly suited for transmitting signals that are within a frequency range of from about 300 megahertz to about 400 megahertz.

The matching element 330 can comprise any suitable material, such as a plastic or other dielectric. The matching element 330 may be flexible and/or compressible, such that at least a lower surface thereof may conform to a contour of the skin of a patient. In various embodiments, one or more matching elements 330 may be used. For example, multiple layers of plastic may be used, in some arrangements.

In some embodiments, a thickness of the matching element 330 is about the same as the depth D to which the antenna assembly 200 is recessed within the cavity 304 of the shield 306. An upper surface of the matching element 330 thus may contact a lower surface of the antenna 204. In some embodiments, the depth D is adjustable so that a secure fit or full contact can be established between the antenna 204 and the matching element 330. For example, in some embodiments, various disposable units 312 having matching elements 330 that differ in thickness may be used with the reusable unit 310, such that an appropriate matching element 330 may be selected to correspond with the anatomy of a specific patient. For example, in some instances, the body mass index (BMI) of a patient may be determined prior to monitoring the core temperature of the patient, and a disposable unit 312 having an appropriately configured matching element 330 may be selected based on the measured BMI. In other embodiments, the characteristics of the matching element 330 may be selected based upon the particular portion of a patient's skin that will be expected to come into contact with the device. In other or further embodiments, the disposable unit 312 may not have an intervening adhesive layer, but rather, may be attached to the patient in another suitable manner. For example, in some embodiments, one or more lengths of tape or any other suitable adhesive (or adhesives) or attachment device (or devices) may be placed about a periphery of the shield extension 320 so as to secure the shield extension 320 to the skin of a patient.

In various embodiments, an adhesive layer 334 may be used to connect at least a portion of the shield extension 320 and/or at least a portion of the matching element 330 to the skin of a patient. In the illustrated embodiment, the adhesive layer 334 comprises a double-sided tape that is connected at an upper surface to both the shield extension 320 and the matching element 330. The bottom surface of the adhesive layer 334 can be attached to the skin of a patient. Any other suitable adhesive materials are possible. The adhesive layer 334 thus can hold the components of the assembly 300 in place and ensure a secure connection to the skin. In some embodiments, an opening is provided in the adhesive layer 334 to permit direct contact between the skin of the patient and at least a portion of the impedance matching layer 330. In other or further embodiments, one or more openings or spaces in the adhesive layer 334 are present at which the shield extension 320 may be in direct contact with the skin of the patient, or at which the patient's skin may be exposed to the matching element and/or shield extension without an intervening adhesive layer.

In some embodiments, one or more components of the disposable unit 312 are permanently attached to each other so as to form a cohesive unit that is readily attached to and detached from the reusable unit 310. For example, in some embodiments, all of the components of the reusable unit 312 shown in FIG. 5 are permanently attached to each other. In other embodiments, one or more components may be selectively attachable to other components of the disposable unit 312. For example, in some embodiments, the conducting paste 324 may be added separately to the shield extension 320 just prior to coupling of the disposable unit 312 with the reusable unit 310. In other or further embodiments, the adhesive layer 334 may be attached to the skin of the patient prior to being coupled to the shield extension 320, or can be attached to the shield extension 320 just prior to being attached to the skin of the patient.

The disposable unit 312 may be selectively connected to the reusable unit 310 via any suitable connection system 350. The connection system 350 may be configured to provide electrical contact between the shield 306 and the shield extension 320, while maintaining a physical connection between the disposable unit 312 and the reusable unit 310. Connection system 350 may also permit ready disconnection of the disposable unit 312 from the reusable unit 310 after use, which can allow for a new disposable unit 312 to be used with the reusable unit 310 thereafter.

In some embodiments, the connection system 350 can comprise a connection interface 351 defined by the shield 306 and a cooperating connection interface 352 defined by any suitable portion of the disposable unit 312. The connection interfaces 351, 352 can be configured to engage with one another so as to temporarily, yet securely, connect the reusable and disposable units 310, 312. In some embodiments, the connection interfaces 351, 352 are complementary to each other. For example, any suitable threading, snapping, or friction-fit system may be used. By way of further example, the connection interface 351 may include an interior surface of the lower end of the shield 306 that is threaded, and the connection interface 352 can include a complementary threaded ring (not shown) that can be coupled with the threaded portion of the shield. In such an arrangement, the reusable unit 310 can be rotated into secure engagement with the disposable unit 312.

In the illustrated embodiment, the connection interface 351 of the reusable unit 310 comprises a lower end of the shield 306, which includes the flange 314. The connection interface 352 of the disposable unit 312 includes an outer perimeter of the matching element 330 and the conducting paste 324. The inner perimeter of the lower end of the shield 306 can be sized to frictionally engage the outer perimeter of the matching element 330 so as to form a friction-tight fit that is sufficient to maintain the disposable unit 312 in connection with the reusable unit 310. Moreover, advancement of the flange 314 into the conducting paste 324 can yield one or more of a suction force and a frictional force that tends to maintain the paste 324 in contact with the flange 314. The connection interfaces 351, 352 can readily disengage from each other upon application of suitable separation forces on the reusable and disposable units 310, 312.

Although the foregoing disclosure identifies a reusable unit 310 and a disposable unit 312, in other embodiments, the assembly 300 may be an integral unit. For example, the entire assembly 300 may be disposable or reusable.

Figure 6:
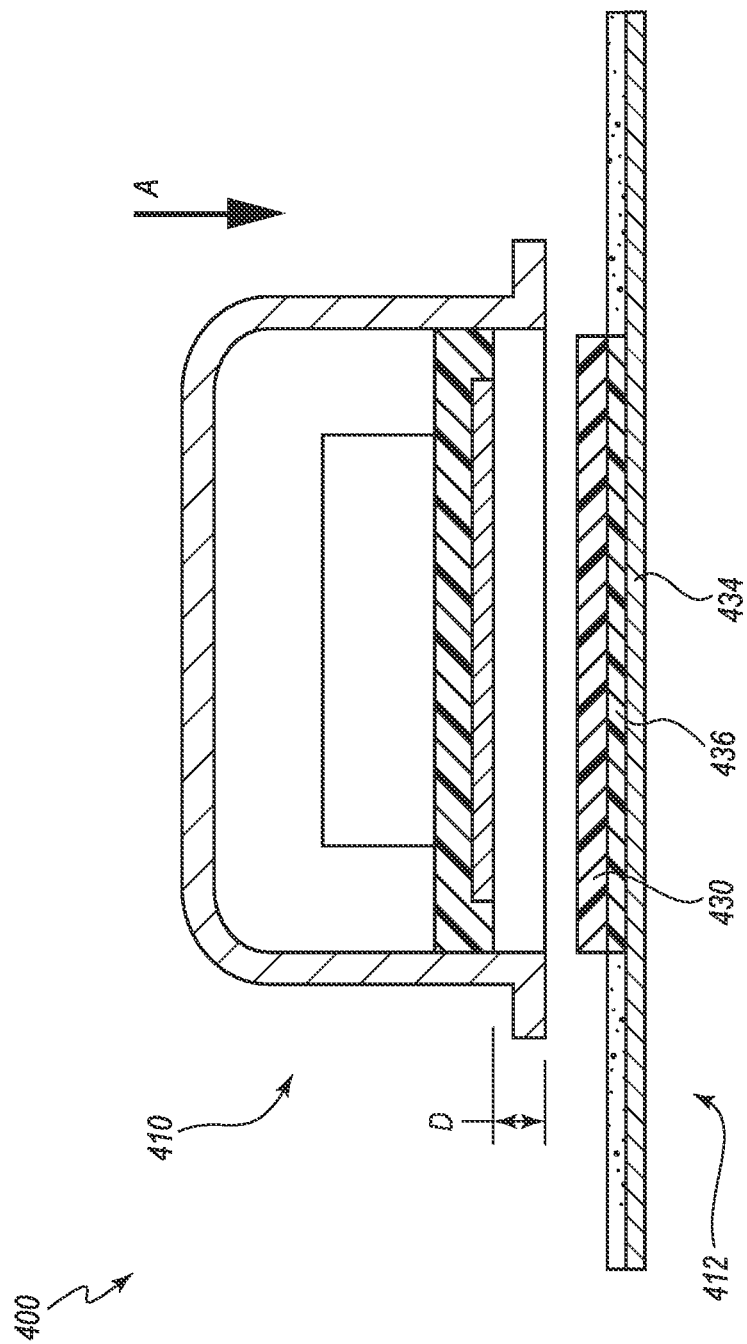
FIG. 6 is a cross-sectional view of another embodiment of a radiometer assembly having a removable unit that includes a matching layer, a bolus, and a shielding extension.

FIG. 6 illustrates another embodiment of a radiometer assembly 400, which resembles the radiometer assembly 300 in many respects. Accordingly, like features are designated with like reference numerals, with the leading digits incremented to "4." Relevant disclosure set forth above regarding similarly identified features thus may not be repeated hereafter. Moreover, specific features of the assembly 400 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the assembly 400. Any suitable combination of the features and variations of the same described with respect to the assembly 300 can be employed with the assembly 400, and vice versa. This pattern of disclosure applies equally to further embodiments depicted in subsequent figures and described hereafter (e.g., the assemblies 500, 600, 700), as well as those discussed previously herein.

The assembly 400 can include a reusable unit 410 and a disposable unit 412. The disposable unit 412 can include a matching element 430, an adhesive layer 434, and a bolus 436. The bolus 436 can be of any suitable variety, and can be configured to conform to a contour of a body to which the system 400 is applied. In the illustrated embodiment, the bolus 436 is formed of a material that is different from that of which the matching element 430 is formed. However, in other embodiments, the bolus 436 and the matching element 430 may be formed from the same material. In still other embodiments (e.g., such as in the embodiment depicted in FIG. 5), the matching element 430 may function as a bolus such that the disposable unit 412 does not include a separate bolus component. As shown in FIG. 6, the depth D may be greater for the assembly 400 than for the assembly 300 so as to accommodate the greater thickness of the matching element 430 and the bolus 436, in combination. FIG. 6 also illustrates an embodiment in which a conducting paste is not used in joining the reusable and disposable units 410, 412.

The bolus 436 may comprise any suitable material, such as, for example, a liquid, gel, or compressible foam. The bolus 436 may be capable of readily changing shape so as to maintain good contact between the skin on one side and the matching element 430 on the other. In some embodiments, the bolus 436 may include active or passive cooling features, such as discussed above, which may be used to cool the skin of the patient in cases where the assembly 400 is operated in a heating mode. The bolus 436 may be relatively thicker or thinner than depicted in FIG. 6. In some embodiments, the bolus 436 comprises water, which in further embodiments, may be actively circulated in manners such as described above with respect to the system 10. The bolus material and/or the thickness thereof can be selected so as to optimize coupling of RF energy into or out of the body 70.

FIG. 7 illustrates another embodiment of a radiometer assembly 500 that includes a reusable unit 510 and a disposable unit 512. The disposable unit 512 includes a layer of one or more metamaterials 538, which in the illustrated embodiment, is disposed between a matching layer 530 and an adhesive layer 534. Other suitable locations for the metamaterial 538 are also possible, although it may be desirable for the metamaterial 538 to be positioned between an antenna 204 and the skin of the patient. The metamaterial 538 can provide "lensing" effects or other phenomena within a given frequency range, which can enhance operation of the antenna 204. For example, the presence of the metamaterial 538 can permit the antenna 204 to be reduced in size without sacrificing its sensitivity to signals received from the patient. Similarly, the metamaterial 538 can focus energy delivered from the antenna 204 to a deep tissue region of the patient with significantly less heating of intermediate tissues, such as the skin. The size, shape, content, and/or one or more other properties of the metamaterial 538 can be selected to provide a desired lensing or focusing effect and/or to optimize coupling of energy into or out of a patient.

In some embodiments, the metamaterial 538 can comprise a flat slab of left-handed metamaterial, which may also be referred to as a flat left-handed metamaterial lens. In some embodiment, the metamaterial lens can be used for receiving energy from the body of a patient, and thus the energy may encounter the metamaterial lens prior to its reception by the antenna 204. In other or further embodiments, the metamaterial lens may be used for hyperthermia treatment in which energy is delivered from the antenna 204 and is altered by the metamaterial lens for delivery into the patient. Such a metamaterial lens may operate in a manner such as that described in Gong et al., "Superficial Tumor Hyperthermia with Flat Left-handed Metamaterial Lens," Progress in Electromagnetics Research, Volume 98, pages 389-405 (2009), the entire contents of which are hereby incorporated by reference herein. Metamaterials used in hyperthermia treatment can reduce the size of energy delivery antennas and can permit energy to be focused at a depth within a patient, thereby reducing skin surface heating.

Figure 8A:
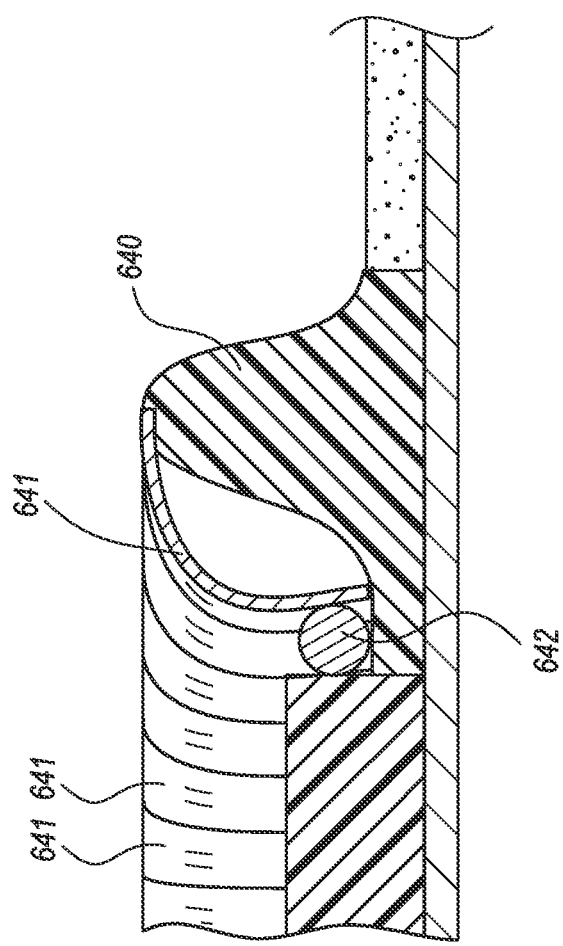
FIG. 8A is an enlarged view of a portion of FIG. 8 taken along the view line 8A.

FIG. 8 illustrates another embodiment of a radiometer assembly 600 that includes a reusable unit 610 and a disposable unit 612. The reusable unit 610 includes a radiometer system 605 (shown schematically), which can include a radiometer and/or an antenna such as those described above. The reusable unit 610 can further include a shield 606 for the radiometer system 605 that is somewhat different from the shield 306. In particular, a lower end of the shield 306 can be configured to couple with the disposable unit 612 differently than the illustrated shield 306 couples with the disposable unit 312, as discussed above.

The illustrated disposable unit 612 includes a conduction ring 640 that is both physically and electrically coupled with a shield extension 620. Other embodiments are also, however, contemplated in which the conduction ring 640 is only physically coupled with the shield extension, or in which the conduction ring is only electrically coupled with the shield extension 620. The conduction ring 640 can comprise any suitable material, and may be sufficiently rigid and/or resilient so as not to distort upon coupling of the shield 606 therewith. For example, in some embodiments, the conduction ring 640 can comprise one or more conductive plastics or foams. In the illustrated embodiment, the conduction ring 640 comprises a phosphor-bronze ring, which can have spring-like properties, and which defines closely spaced resilient fingers 641 that extend about a periphery thereof (see FIG. 8A). Such an arrangement can permit the shield 606 to be hand-pressed into the disposable unit 612 and hand-removed therefrom. Other coupling arrangements are also contemplated.

Stated otherwise, the disposable unit 612 can be selectively connected to the reusable unit 610 via a connection system 650 that resembles the connection system 350 depicted in FIG. 5 in certain respects, but varies from it in others. As with the connection system 350, the connection system 650 is configured to provide electrical contact between the shield 606 and the shield extension 620, while maintaining a physical connection between the disposable unit 612 and the reusable unit 610. Moreover, the connection system 650 permits ready disconnection of the disposable unit 612 from the reusable unit 610 after use, which can allow for a new disposable unit 612 to be used with the reusable unit 610 thereafter.

However, the connection system 650 comprises a connection interface 651 of the reusable unit 610 that includes a lower end of the shield 606, which has a different configuration than the lower end of the shield 306. In particular, in the illustrated embodiment, the lower end of the shield 606 does not include a flange. Rather, the outer surface of the shield 606 can be substantially cylindrically shaped, and may be smooth. The connection interface 652 of the disposable unit 612 includes the resilient fingers 641, which define a substantially cylindrical shape that has a slightly smaller diameter than the outer diameter of the lower end of the shield 606. Accordingly, advancement of the lower end of the shield 606 into contact with the resilient fingers 641 forces the fingers 641 outward, which gives rise to a restorative force in the fingers 641 that tends to grip the shield 606 and hold it in fixed relation relative to the disposable unit 612. The connection interfaces 651, 652 can readily disengage from each other upon application of suitable separation forces on the reusable and disposable units 610, 612.

In some embodiments, the disposable unit 612 can include an radiofrequency (RF) or electromagnetic interference (EMI) gasket 642, which can extend about an interior of the conduction ring 640 and can be securely coupled therewith. The EMI gasket 642 can assist in forming a EMI-tight seal between the disposable unit 612 and the reusable unit 610. Other arrangements are also possible. For example, in some embodiments, an EMI gasket can be included at a lower end of the shield 606 instead of or in addition to the EMI gasket 642 of the disposable unit 612.

In the illustrated embodiment, the EMI gasket 642 encompasses a matching layer 630. The disposable unit 612 can further include an adhesive layer 634, which can be similar to the adhesive layers discussed above.

Figure 9:
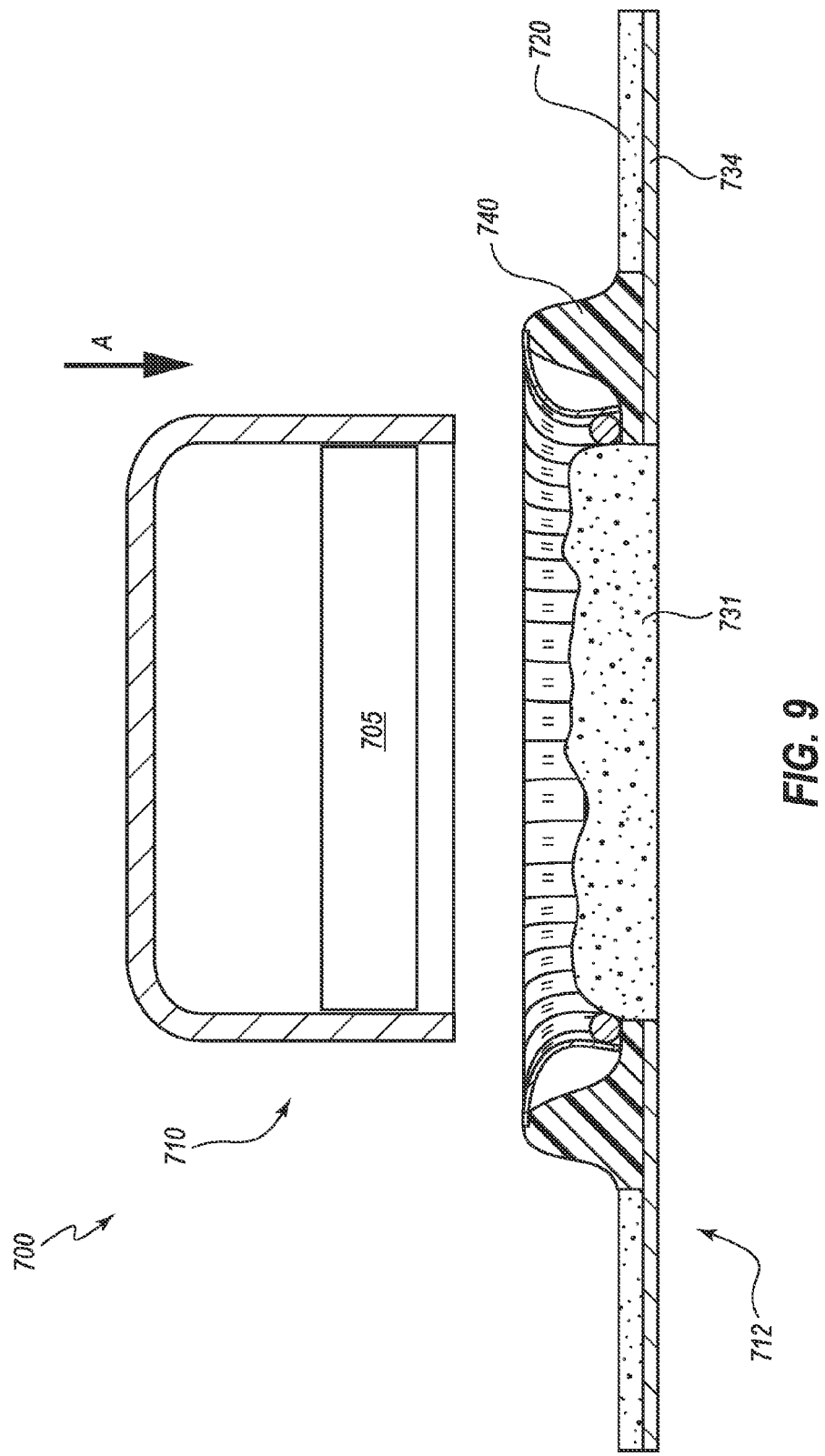
FIG. 9 is a cross-sectional view of another embodiment of a radiometer assembly that includes another embodiment of a removable unit.

FIG. 9 illustrates another embodiment of a radiometer assembly 700 that includes a reusable unit 710 and a disposable unit 712. The reusable unit 710 includes a radiometer system 705. The disposable unit 712 includes a conducting ring 740 that can be coupled with the reusable unit 710 in a manner such as described above. The disposable unit 712 can further include a shielding extension 720 and an adhesive layer 734 similar to those discussed above.

A matching material 731 can be used with the assembly 700. In the illustrated embodiment, the matching material 731 comprises one or more of a gel, jelly, or semi-gelatin material that can coat, cover, or otherwise contact a bottom end of the radiometer system 705 and can further coat, cover, or otherwise cover a portion of the skin of a patient that is encompassed by the conducting ring 740. The matching material 731 can act as both a bolus and an impedance or RF matching material. In some embodiments, the matching material 731 can comprise a double-sided adhesive, which may have any of a variety of thicknesses, strengths, and/or stickinesses. Suitable double-sided adhesives are available from 3M of St. Paul, Minn.

FIG. 10 illustrates another embodiment of a radiometer assembly 800 that includes a reusable unit 810 and a disposable unit 812. In the illustrated embodiment, the radiometer assembly 800 closely resembles the radiometer assembly 700 depicted in FIG. 9. However, other arrangements are also possible, such as those depicted in FIGS. 5-8 and discussed with respect thereto.

In the illustrated embodiment, the reusable unit 810 includes a radiometer system 805 that is positioned within a shield 806, and the disposable unit 812 includes a conducting ring 840 and an EMI gasket 842, such as those described above. The disposable unit 812 can be coupled with the reusable unit 810 in any suitable manner, such as those described above The disposable unit 812 can further include a power source 860, which can be configured to provide power to the radiometer system 805 during use of the radiometer assembly 800. For example, in some embodiments, the power source 860 can include one or more batteries of any suitable variety. Any other suitable arrangement for the power source 860 is possible.

In the illustrated embodiment, the power source 860 is electrically coupled with a connector 862 via an electrical lead 864, each of which can be mounted to any suitable portion of the disposable unit 812. Similarly, the radiometer system 805 can be electrically coupled with a connector 866 via an electrical lead 868. The connectors 862, 866 can be configured to electrically engage with each other when the reusable unit 810 is coupled with the disposable unit 812.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers.

Any suitable combination of the various features of the disclosed embodiments is contemplated. Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

The invention claimed is:

1. A system for monitoring an internal temperature of a patient, the system comprising:
    an electrical shield that defines a cavity having an opening at an end thereof, wherein the electrical shield comprises a connection interface;
    a radiometer, wherein at least a portion of the radiometer is positioned within the cavity of the shield so as to be protected from stray electromagnetic radiation;
    an antenna coupled with the radiometer and positioned within the cavity of the shield, wherein the antenna is recessed within the cavity; and
    a disposable unit configured to selectively cover the opening of the cavity, wherein the disposable unit comprises:
        an impedance matching element configured to couple electromagnetic energy into or out of the antenna, wherein the impedance matching element is configured to be positioned within the cavity when the disposable unit is coupled with the electrical shield such that the impedance matching element can contact the antenna;
        a shield extension configured to extend beyond a perimeter of the electrical shield when the disposable unit is coupled with the electrical shield so as to further protect the at least a portion of the radiometer that is positioned within the cavity of the shield from stray electromagnetic radiation; and
        a connection interface that is configured to be selectively coupled with the electrical shield.

2. The system of claim 1, wherein the impedance matching element, the shield extension, and the connection interface are permanently attached to each other such that the disposable unit can be attached to and removed from the electrical shield as a cohesive unit.

3. The system of claim 1, wherein the disposable unit comprises a strip of conducting paste in electrical contact with the shield extension, wherein the strip of conducting paste is configured to contact a lower end of the electrical shield about a full periphery thereof when the disposable unit is coupled with the electrical shield.

4. The system of claim 1, wherein the connection interface of the disposable unit comprises an outer edge of the matching element that is configured to frictionally engage an inner surface of the electrical shield when the disposable unit is coupled with the electrical shield.

5. The system of claim 1, wherein the connection interface of the disposable unit comprises a series of resilient fingers that are configured to grip a lower end of the electrical shield when the disposable unit is coupled with the electrical shield.

6. The system of claim 1, wherein the disposable unit further comprises an adhesive layer attached to the shield extension, wherein the adhesive layer is configured to attach the shield extension to the skin of a patient.

7. The system of claim 1, wherein the impedance matching element is coupled to a bolus that is configured to conform to a contour of the skin of a patient.

8. The system of claim 1, wherein the disposable unit further comprises a layer of metamaterial.

9. The system of claim 1, wherein the disposable unit further comprises a conduction ring electrically coupled with the shield extension, wherein the conduction ring is configured to receive a lower end of the electrical shield when the disposable unit is coupled with the electrical shield.

10. The system of claim 9, wherein the disposable unit further comprises an electromagnetic interference gasket in electrical contact with the conduction ring, wherein the electromagnetic interference gasket is configured to be compressed between a portion of the conduction ring and a portion of the electrical shield when the disposable unit is coupled with the electrical shield.

11. The system of claim 1, wherein the impedance matching element comprises a layer of matching material that comprises one or more of a gel, jelly, or semi-gelatin material that is configured to contact the antenna when the disposable unit is coupled with the electrical shield.

12. The system of claim 1, further comprising an additional disposable unit configured to selectively cover the opening of the cavity, wherein the additional disposable unit comprises:
    an additional impedance matching element configured to couple electromagnetic energy into or out of the antenna, wherein the additional impedance matching element defines one or more of a thickness, density, and dielectric constant that differs from that of the impedance matching element such that the additional impedance matching element can couple electromagnetic energy into or out of the antenna in a different manner, as compared with the impedance matching element;
    an additional shield extension configured to extend laterally outward from the electrical shield when the disposable unit is coupled with the electrical shield so as to further protect the at least a portion of the radiometer that is positioned within the cavity of the shield from stray electromagnetic radiation; and
    an additional connection interface that is configured to be selectively coupled with the electrical shield.

13. The system of claim 1, further comprising a power source configured to provide power to the radiometer.

14. The system of claim 13, wherein the disposable unit comprises the power source and an electrical connector coupled with the power source, wherein the electrical shield comprises an electrical connector coupled with the radiometer, and wherein the electrical connectors are configured to electrically couple with each other when the disposable unit is coupled with the electrical shield.

15. A system for monitoring an internal temperature of a patient, the system comprising:
    an electrical shield that defines a cavity having an opening at an end thereof, wherein the electrical shield comprises a connection interface;
    a radiometer, wherein at least a portion of the radiometer is positioned within the cavity of the shield so as to be protected from stray electromagnetic radiation;
    an antenna assembly positioned within the cavity of the electrical shield, the antenna assembly comprising:
        an antenna coupled with the radiometer and positioned within the cavity of the shield; and
        a substrate coupled with the antenna such that at least a portion of the antenna is exposed to the opening of the electrical shield;

an impedance matching element in contact with the antenna, wherein the impedance matching element is configured to couple electromagnetic energy into or out of the antenna; and a shield extension that is electrically coupled with and extends from the electrical shield so as to further protect the at least a portion of the radiometer that is positioned within the cavity of the shield from stray electromagnetic radiation.

16. The system of claim 15, wherein the shield extension is flexible so as to be able to conform to a contour of the skin of a patient.

* * * * *